(12) United States Patent
Vojkovsky et al.

(10) Patent No.: US 7,037,909 B2
(45) Date of Patent: May 2, 2006

(54) TETRACYCLIC COMPOUNDS AS C-MET INHIBITORS

(75) Inventors: Tomas Vojkovsky, San Francisco, CA (US); Marcel Koenig, Boca Raton, FL (US); Fang-Jie Zhang, Sunnyvale, CA (US); Jingrong Cui, San Diego, CA (US)

(73) Assignee: Sugen, Inc., San Diego, CA (US)

( * ) Notice: Subject to any disclaimer, the term of this patent is extended or adjusted under 35 U.S.C. 154(b) by 172 days.

(21) Appl. No.: 10/878,632

(22) Filed: Jun. 29, 2004

(65) Prior Publication Data

US 2005/0014755 A1 Jan. 20, 2005

Related U.S. Application Data

(60) Provisional application No. 60/484,222, filed on Jul. 2, 2003.

(51) Int. Cl.
*C07D 487/04* (2006.01)
*C07D 487/14* (2006.01)
*A61K 31/53* (2006.01)

(52) U.S. Cl. ...................................... 514/243; 544/184
(58) Field of Classification Search ................. 544/184, 544/243; 514/243
See application file for complete search history.

(56) References Cited

U.S. PATENT DOCUMENTS

| 4,084,053 A | 4/1978 | Desai et al. |
| 4,159,375 A | 6/1979 | Trust et al. |
| 4,405,619 A | 9/1983 | Heilman et al. |

FOREIGN PATENT DOCUMENTS

| NL | 6410715 | 3/1965 |
| WO | WO 96/18770 A2 | 6/1996 |
| WO | WO 97/48786 A1 | 12/1997 |
| WO | WO 99/01607 A2 | 1/1999 |

OTHER PUBLICATIONS

Cecil Textbook of Medicine, edited by Bennet, J.C., and Plum F., 20th edition,vol. 1, 1004–1010, 1996.*
Knudsen et al. Adv Cancer Res. 91: 31–67, 2004.*
Elliott et al. Can. J. Physiol. Pharmacol. 80(2) : 91–102, 2002.*
Dornow et al., "Desaminierung von 4–Amino–1.2.4–triazinen," *Chemische Berichte*, Sep. 1964, pp. 2647–2651, vol. 97, No. 9.
Dornow et al., "Übert Umsetzungen von a–Chlor–oximen. II²," *Chemische Berichte*, 1964, pp. 2165–2168, vol. 97, No. 8.
Labouta et al., "Synthesis of Some Substituted Triazolo[4,3–b][1,2,4]triazines as Potential Anticancer Agents," *Monatshefte für Chemie*, 1988, pp. 591–596, vol. 119.

Lovell et al., "6– An 7–Aryl–1,2,4–triazolo[4,3–b]–1,2,4–triazines. Synthesis and Characterization (1)," *Journal of Heterocyclic Chemistry*, Nov. 1979, pp. 1393–1403, vol. 16, No. 7.
Mousaad et al., "Synthesis of 3–(Alditol–1–yl)triazolo[4',3':2,3]–1,2,4–triazno[5,6–b]indoles," *Bull. Chem. Soc. Jpn.*, 1992, pp. 546–552, vol. 65, No. 2, The Chemical Society of Japan.
Rahman, "Synthesis of Some More Heterobicyclic Derivatives Bearing A 1,2,4–Triazine Moiety and Their Antibacterial Activity," *Pakistan Journal of Scientifici and Industrial Research*, Apr. 1989, pp. 240–245, vol. 32, No. 4, Pakistan Council of Scientific and Industrial Research Karachi.
Rashed et al., "10–Carbethoxymethyl–3–phenyl–1,2,4–triazolo[4',3':2,3][1,2,4]triazino [5,6–b]indole and Derivatives at its 10–Position," *Archiv der Pharmazie*, Mar. 1993, pp. 153–156, vol. 326, No. 3, VCH.

(Continued)

*Primary Examiner*—Venkataraman Balasubramanian
(74) *Attorney, Agent, or Firm*—Bryan C. Zielinski; Vincent P. Liptak

(57) ABSTRACT

The present invention relates to compounds of the Formulae (I) and (II), wherein $R_1$–$R_{10}$ and G are defined herein, and their pharmaceutically acceptable salts. These compounds modulate the activity of c-Met and are therefore expected to be useful in the prevention and treatment of c-Met related disorders such as cancer.

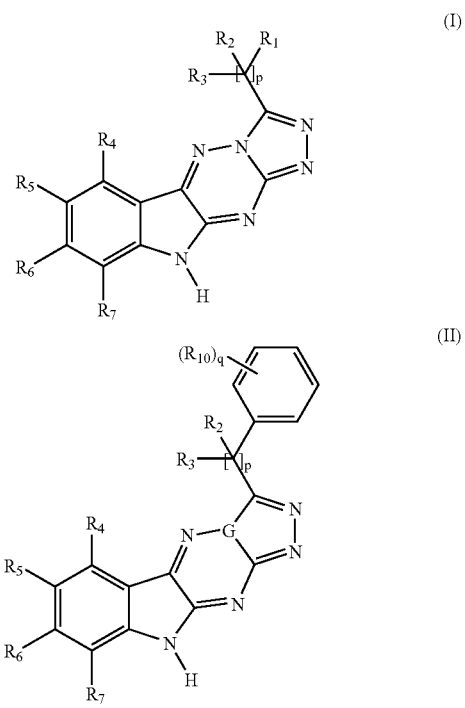

11 Claims, No Drawings

OTHER PUBLICATIONS

Shaban et al., "Sterically controlled regiospecific heterocyclization of 3–hydrazino–5–methyl–1,2,4–triazino[5,6–a]indole to 10–methyl–1,2,4–triazolo[4',3':2,3]1,2,4–triazino[5,6–b]indoles," *Il Farmaco*, 1999, pp. 800–809, vol. 54, Elsevier.

Tomchin, *Zhurnal Organicheskoi Kimii*, 1982, pp. 1272–1280, vol. 18, No. 6.

Vlietinck, "Triazolotriazines as Potential Chemoterapeutic Agents. IV." *Journal of Heterocyclic Chemistry*, Sep.–Oct. 1987, vol. 24, No. 5.

Zaher et al., "uncondensed 1,2,4–Triazines: Part I—Behaviour of 3–Hydrazino–5,6,–diphenyl–1,2,4–triazine Towards Acylating Agents, Activated Alkenes & Carbonyl Compounds," *Indian Journal of Chemistry*, Oct. 1979, pp. 316–319, vol. 18B.

* cited by examiner

TETRACYCLIC COMPOUNDS AS C-MET INHIBITORS

This application claims the benefit of U.S. Provisional Application Ser. No. 60/484,222, filed Jul. 2, 2003, the disclosure of which is incorporated herein by reference in its entirety.

BACKGROUND OF THE INVENTION

The following is offered as background information only and is not admitted to be prior art to the present invention.

Protein kinases ("PKs") are enzymes that catalyze the phosphorylation of hydroxy groups on tyrosine, serine and threonine residues of proteins. The consequences of this seemingly simple activity are staggering; cell growth, differentiation and proliferation, i.e., virtually all aspects of cell life in one way or another depend on PK activity. Furthermore, abnormal PK activity has been related to a host of disorders, ranging from relatively non-life threatening diseases such as psoriasis to extremely virulent diseases such as glioblastoma (brain cancer).

The PKs can be conveniently broken down into two classes, the protein tyrosine kinases (PTKs) and the serine-threonine kinases (STKs).

One of the prime aspects of PTK activity is their involvement with growth factor receptors. Growth factor receptors are cell-surface proteins. When bound by a growth factor ligand, growth factor receptors are converted to an active form which interacts with proteins on the inner surface of a cell membrane. This leads to phosphorylation on tyrosine residues of the receptor and other proteins and to the formation inside the cell of complexes with a variety of cytoplasmic signaling molecules that, in turn, effect numerous cellular responses such as cell division (proliferation), cell differentiation, cell growth, expression of metabolic effects to the extracellular microenvironment, etc. For a more complete discussion, see Schlessinger and Ullrich, *Neuron* 9:303–391 (1992), which is incorporated by reference, including any drawings, as if fully set forth herein.

Growth factor receptors with PTK activity are known as receptor tyrosine kinases ("RTKs"). They comprise a large family of transmembrane receptors with diverse biological activity. At present, at least nineteen (19) distinct subfamilies of RTKs have been identified. An example of these is the subfamily designated the "HER" RTKs, which include EGFR (epithelial growth factor receptor), HER2, HER3 and HER4. These RTKs consist of an extracellular glycosylated ligand binding domain, a transmembrane domain and an intracellular cytoplasmic catalytic domain that can phosphorylate tyrosine residues on proteins.

Another RTK subfamily consists of insulin receptor (IR), insulin-like growth factor I receptor (IGF-1R) and insulin receptor related receptor (IRR). IR and IGF-1R interact with insulin, IGF-I and IGF-II to form a heterotetramer of two entirely extracellular glycosylated subunits and two subunits which cross the cell membrane and which contain the tyrosine kinase domain.

A third RTK subfamily is referred to as the platelet derived growth factor receptor ("PDGFR") group, which includes PDGFR, CSFIR, c-kit and c-fms. These receptors consist of glycosylated extracellular domains composed of variable numbers of immunoglobin-like loops and an intracellular domain wherein the tyrosine kinase domain is interrupted by unrelated amino acid sequences.

Another group which, because of its similarity to the PDGFR subfamily, is sometimes subsumed into the later group is the fetus liver kinase ("flk") receptor subfamily. This group is believed to be made of up of kinase insert domain-receptor fetal liver kinase-1 (KDR/FLK-1), flk-1R, flk-4 and fms-like tyrosine kinase 1 (flt-1). Still another member of the growth factor receptor family is the vascular endothelial growth factor ("VEGF") receptor subgroup. VEGF is a dimeric glycoprotein similar to PDGF but has different biological functions and target cell specificity in vivo. In particular, VEGF is presently thought to play an essential role is vasculogenesis and angiogenesis.

A further member of the tyrosine kinase growth factor receptor family is the fibroblast growth factor ("FGF") receptor subgroup. This group consists of four receptors, FGFR1–4, and seven ligands, FGF1–7. While not yet well defined, it appears that the receptors consist of a glycosylated extracellular domain containing a variable number of immunoglobin-like loops and an intracellular domain in which the tyrosine kinase sequence is interrupted by regions of unrelated amino acid sequences.

Still another member of the tyrosine kinase growth factor receptor family is MET, often referred to as c-Met. c-met is also known as hepatocyte growth factor receptor or scatter factor receptor. c-Met is thought to play a role in primary tumor growth and metastasis.

A more complete listing of the known RTK subfamilies is described in Plowman et al., DN&P, 7(6):334–339 (1994), which is incorporated by reference, including any drawings, as if fully set forth herein.

In addition to the RTKs, there also exists a family of entirely intracellular PTKs called "non-receptor tyrosine kinases" or "cellular tyrosine kinases." This latter designation, abbreviated "CTK," will be used herein. CTKs do not contain extracellular and transmembrane domains. At present, over 24 CTKs in 11 subfamilies (Src, Frk, Btk, Csk, Abl, Zap70, Fes, Fps, Fak, Jak and Ack) have been identified. The Src subfamily appear so far to be the largest group of CTKs and includes Src, Yes, Fyn, Lyn, Lck, Blk, Hck, Fgr and Yrk. For a more detailed discussion of CTKs, see Bolen, *Oncogene*, 8:2025–2031 (1993), which is incorporated by reference, including any drawings, as if fully set forth herein.

The serine/threonine kinases, STKs, like the CTKs, are predominantly intracellular although there are a few receptor kinases of the STK type. STKs are the most common of the cytosolic kinases; i.e., kinases that perform their function in that part of the cytoplasm other than the cytoplasmic organelles and cytoskelton. The cytosol is the region within the cell where much of the cell's intermediary metabolic and biosynthetic activity occurs; e.g., it is in the cytosol that proteins are synthesized on ribosomes.

RTKs, CTKs and STKs have all been implicated in a host of pathogenic conditions including, significantly, cancer. Other pathogenic conditions which have been associated with PTKs include, without limitation, psoriasis, hepatic cirrhosis, diabetes, angiogenesis, restenosis, ocular diseases, rheumatoid arthritis and other inflammatory disorders, immunological disorders such as autoimmune disease, cardiovascular disease such as atherosclerosis and a variety of renal disorders.

With regard to cancer, two of the major hypotheses advanced to explain the excessive cellular proliferation that drives tumor development relate to functions known to be PK regulated. That is, it has been suggested that malignant cell growth results from a breakdown in the mechanisms that control cell division and/or differentiation. It has been shown that the protein products of a number of proto-oncogenes are involved in the signal transduction pathways that regulate cell growth and differentiation. These protein products of proto-oncogenes include the extracellular growth factors, transmembrane growth factor PTK receptors (RTKs), cytoplasmic PTKs (CTKs) and cytosolic STKs, discussed above.

In view of the apparent link between PK-related cellular activities and wide variety of human disorders, it is no surprise that a great deal of effort is being expended in an attempt to identify ways to modulate PK activity. Some of these have involved biomimetic approaches using large molecules patterned on those involved in the actual cellular processes (e.g., mutant ligands (U.S. application Ser. No. 4,966,849); soluble receptors and antibodies (Application No. WO 94/10202, Kendall and Thomas, *Proc. Nat'l Acad. Sci.*, 90:10705–10709 (1994), Kim, et al., *Nature*, 362:841–844 (1993)); RNA ligands (Jelinek, et al., *Biochemistry*, 33:10450–56); Takano, et al., *Mol. Bio. Cell*, 4:358A (1993); Kinsella, et al., *Exp. Cell Res.*, 199:56–62 (1992); Wright, et al., *J. Cellular Phys.*, 152:448–57) and tyrosine kinase inhibitors (WO 94/03427; WO 92/21660; WO 91/15495; WO 94/14808; U.S. Pat. No. 5,330,992; Mariani, et al., *Proc. Am. Assoc. Cancer Res.*, 35:2268 (1994)).

In addition to the above, attempts have been made to identify small molecules which act as PK inhibitors. For example, bis-monocylic, bicyclic and heterocyclic aryl compounds (PCT WO 92/20642), vinylene-azaindole derivatives (PCT WO 94/14808) and 1-cyclopropyl-4-pyridylquinolones (U.S. Pat. No. 5,330,992) have been described as tyrosine kinase inhibitors. Styryl compounds (U.S. Pat. No. 5,217,999), styryl-substituted pyridyl compounds (U.S. Pat. No. 5,302,606), quinazoline derivatives (EP Application No. 0 566 266 A1), selenaindoles and selenides (PCT WO 94/03427), tricyclic polyhydroxylic compounds (PCT WO 92/21660) and benzylphosphonic acid compounds (PCT WO 91/15495) have all been described as PTK inhibitors useful in the treatment of cancer.

SUMMARY OF THE INVENTION

The invention relates to a compound of the formula I:

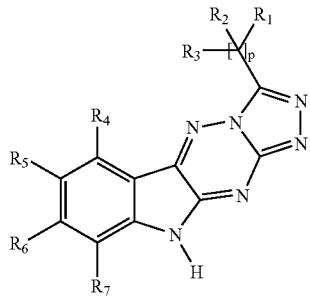

wherein:
$R_1$ is an aryl or heteroaryl group, wherein said aryl or heteroaryl group is unsubstituted or optionally substituted with one or more substituents selected from the group consisting of halogen, —OH, —OR$_8$, —COR$_8$, —COOR$_8$, —CONR$_8$R$_9$, —NR$_8$R$_9$, —CN, —NO$_2$, —S(O)$_2$R$_8$, —SO$_2$NR$_8$R$_9$, —CF$_3$, lower alkyl, cycloalkyl, heterocycle, alkenyl, alkynyl and aryl;

each $R_2$ and $R_3$ is independently selected from the group consisting of hydrogen, halogen, —OH, —OR$_7$, —NR$_7$R$_8$, —CN, —COR$_8$, —COOR$_8$, —CONR$_8$R$_9$, —CF$_3$, lower alkyl, cycloalkyl, heterocycle, alkenyl and alkynyl; or $R_2$ and $R_3$, together with the carbon atom to which they are attached can form a cycloalkyl or heterocycle;

$R_4$, $R_5$, $R_6$, and $R_7$ are independently selected from the group consisting of hydrogen, halogen, —OR$_8$, —COR$_8$, —COOR$_8$, —CONR$_8$R$_9$, —NR$_8$R$_9$, —CN, —NO$_2$, —S(O)$_n$R$_6$ (wherein n is 0, 1 or 2), —SO$_2$R$_7$R$_8$, —CF$_3$, lower alkyl, cycloalkyl, heterocycle, alkenyl, alkynyl, and aryl; and each $R_8$ and $R_9$ is independently selected from the group consisting of hydrogen, lower alkyl, cycloalkyl, heterocycle, allkenyl, alkynyl, aryl, aminoalkyl, alkylaminoalkyl, dialkylaminoalkyl or $R_8$ and $R_9$ together with the atom to which they are attached form a heteroalicyclic ring optionally substituted with a group selected from the group consisting of alkyl, —OH and amino; and p is 1, 2, 3, 4 or 5, it being understood that when p is an integer greater than 1, the $R_2$ and $R_3$ groups on each carbon atom may be the same as or different from the $R_2$ and $R_3$ groups on any adjacent carbon atom; or a pharmaceutically acceptable salt thereof.

In a preferred embodiment, the variable p in a compound of formula I is 1.

In another preferred embodiment, the aryl group on the compound of formula I is phenyl.

In still another preferred embodiment the aryl group on the compound of formula I is a phenyl group substituted with an —OH or a halo group.

The invention further relates to a compound of formula II:

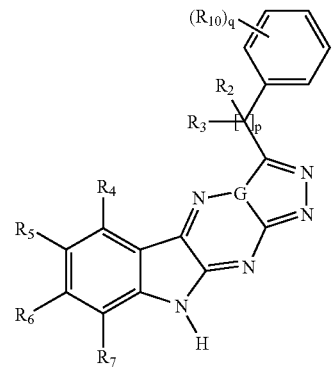

wherein:
each $R_{10}$ is independently selected from the group consisting of halogen, —OH, —OR$_8$, —COR$_8$, —COOR$_8$, —CONR$_8$R$_9$, —NR$_8$R$_9$, —CN, —NO$_2$, —S(O)$_2$R$_8$, —SO$_2$NR$_8$R$_9$, —CF$_3$, lower alkyl, cycloalkyl, heterocycle, alkenyl, alkynyl and aryl;

q is 1, 2, 3, 4 or 5;

G is nitrogen or carbon;

each $R_2$ and $R_3$ is independently selected from the group consisting of hydrogen, halogen, —OH, —OR$_7$, —NR$_7$R$_8$, —CN, —COR$_8$, —COOR$_8$, —CONR$_8$R$_9$, —CF$_3$, lower alkyl, cycloalkyl, heterocycle, alkenyl and alkynyl; or $R_2$ and $R_3$, together with the carbon atom to which they are attached can form a cycloalkyl or heterocycle;

$R_4$, $R_5$, $R_6$, and $R_7$ are independently selected from the group consisting of hydrogen, halogen, —OR$_8$, —COR$_8$, —COOR$_8$, —CONR$_8$R$_9$, —NR$_8$R$_9$, —CN, —NO$_2$, —S(O)$_n$R$_8$ (wherein n is 0, 1 or 2), —SO$_2$R$_8$R$_9$, —CF$_3$, lower alkyl, cycloalkyl, heterocycle, alkenyl, alkynyl, and aryl; and R$_8$ and R$_9$ are selected from the group consisting of hydrogen, lower alkyl, cycloalkyl, heterocycle, alkenyl, alkynyl, aryl, aminoalkyl, alkylaminoalkyl, and dialkylaminoalkyl or R$_8$ and R$_9$ together with the atom to which they are attached form a heteroalicyclic ring optionally substituted with a group selected from the group consisting of alkyl, —OH and amino; and p is 1, 2, 3, 4 or 5, it being understood that when p is an integer greater than 1, the R$_2$ and R$_3$ groups on each carbon atom may be the same as or different from the R$_2$ and R$_3$ groups on any adjacent carbon atom; or a pharmaceutically acceptable salt thereof.

In a preferred embodiment, the variable p in the compound of formula II is 1.

In another preferred embodiment, R$_{10}$ in the compound of formula II is —OH or halo and q is 1.

In still another preferred embodiment, the variable G in the compound of formula II is nitrogen.

In yet another preferred embodiment, the compound of formula I or II is a compound selected from the group consisting of:

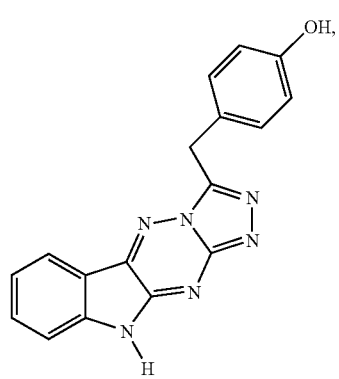

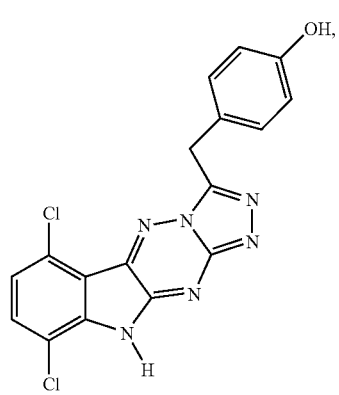

-continued

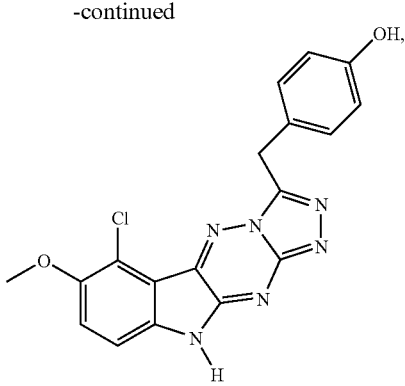

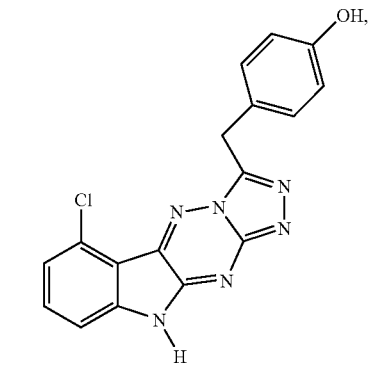

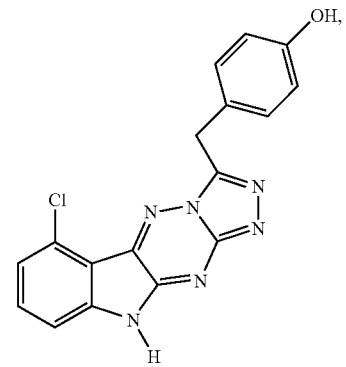

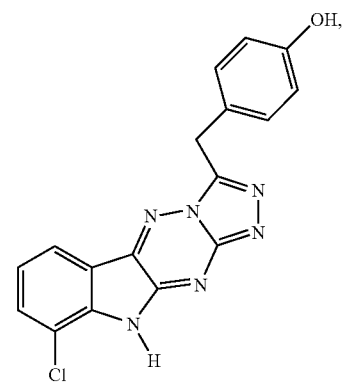

-continued
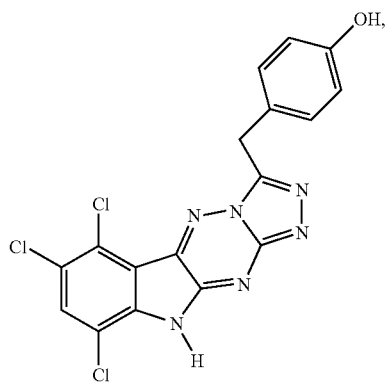
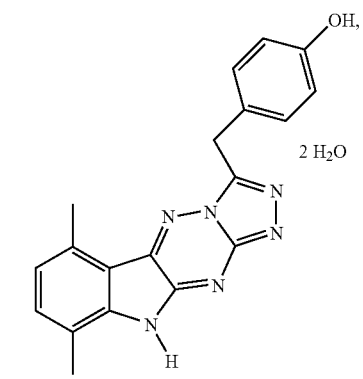
2 H₂O
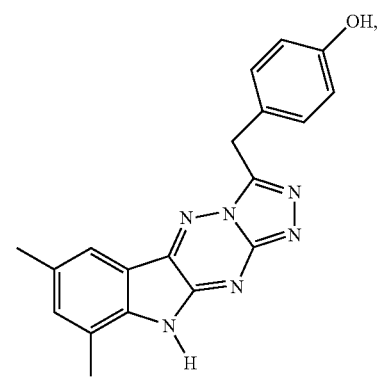
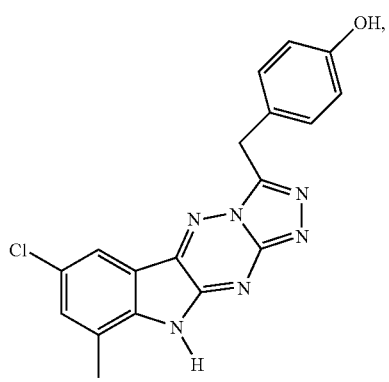
-continued
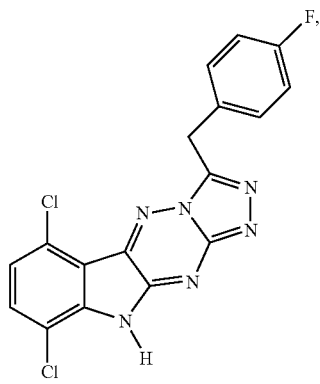
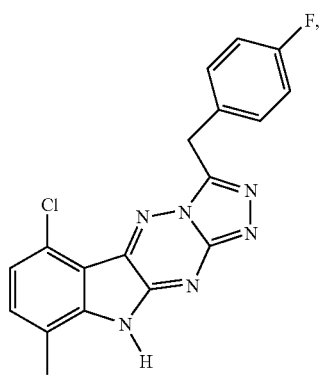
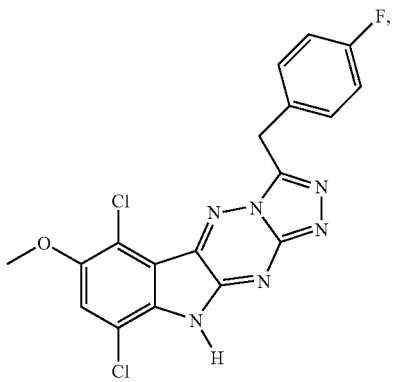
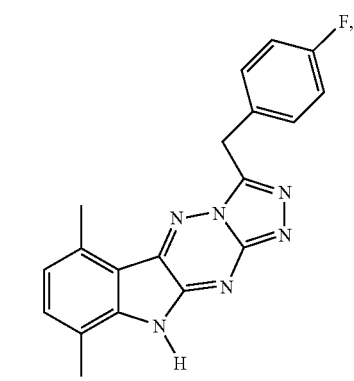

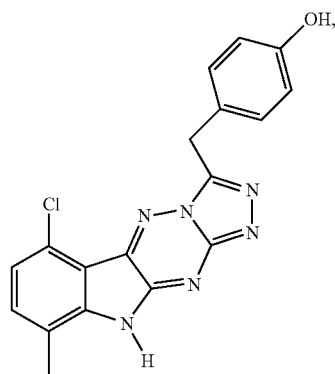
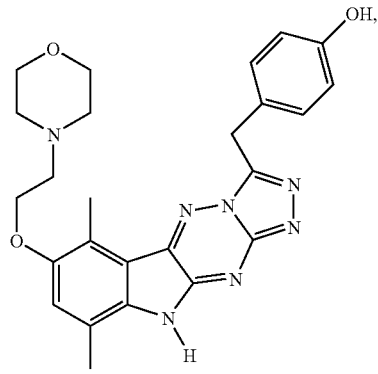
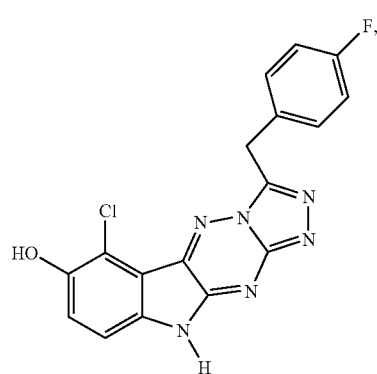
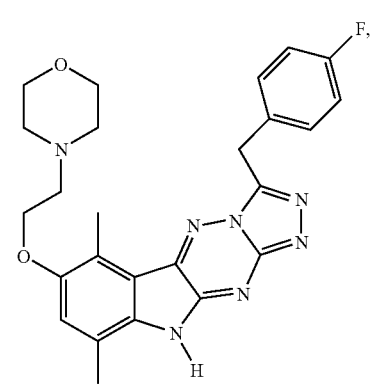
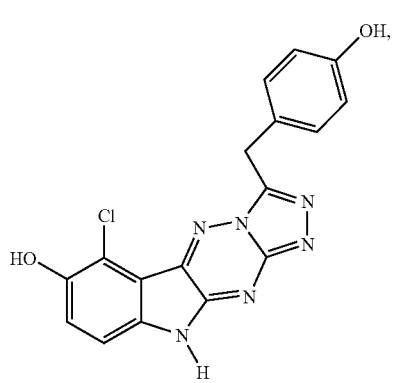
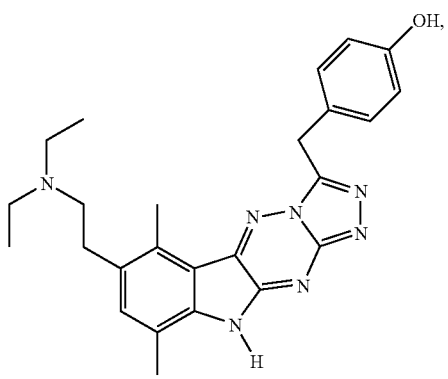
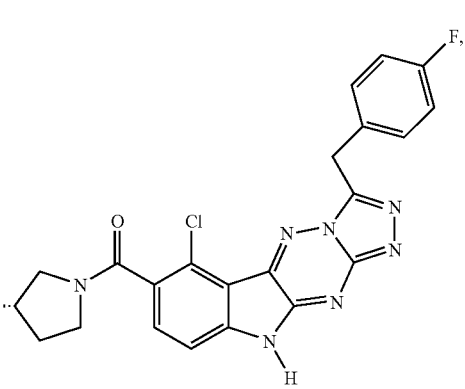
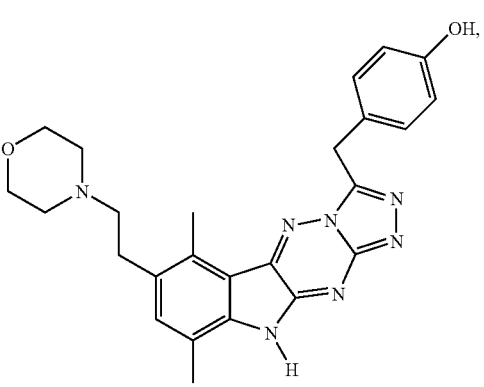

-continued

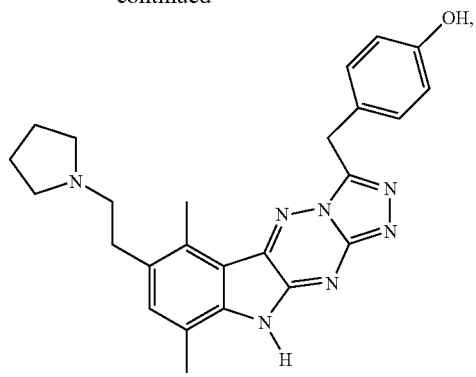

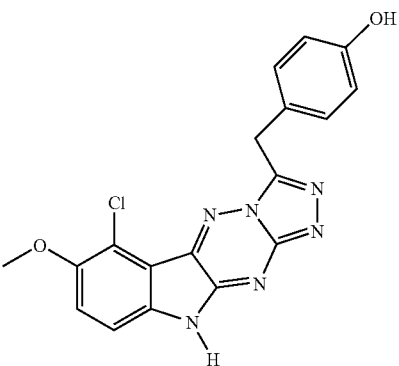

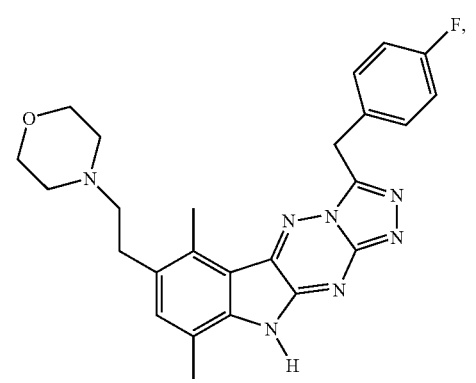

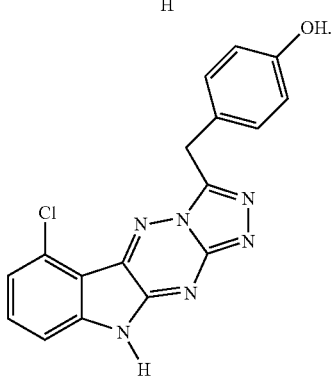

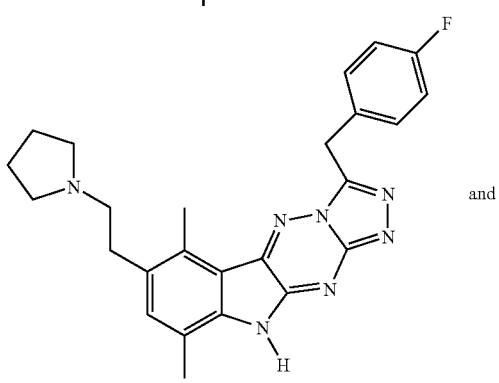

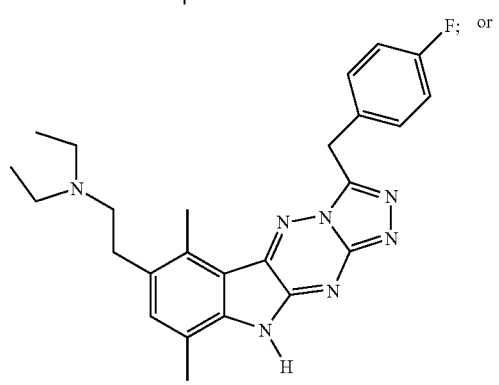

a pharmaceutically acceptable salt thereof.

In still another preferred embodiment, the compound of formula I or II is:

The invention further relates to a method for treating a c-Met related disorder with a compound of formula I or II.

In a preferred embodiment, the c-Met related disorder is a cancer.

In another preferred embodiment, the cancer is selected from the group consisting of breast cancer, lung cancer, colorectal cancer, prostate cancer, pancreatic cancer, glioma, liver cancer, gastric cancer, head cancer, neck cancer, melanoma, renal cancer, leukemia, myeloma, and sarcoma.

The invention still further relates to a pharmaceutical composition comprising a compound of formula I or II or pharmaceutically acceptable salt thereof, and a pharmaceutically acceptable carrier or excipient.

DETAILED DESCRIPTION OF THE PREFERRED EMBODIMENTS

A family of novel tetracyclic compounds have been discovered which exhibit c-Met modulating ability and have a ameliorating effect against disorders related to abnormal c-Met activity. c-Met is an attractive target from a clinical perspective because: 1) c-Met has been implicated in the growth and metastases of most types of cancer; 2) growth at the secondary site appears to be the rate-limiting step in metastasis; and 3) by the time of diagnosis, it is likely that the disease has already spread.

c-Met is a receptor tyrosine kinase that is encoded by the Met protooncogene and transduces the biological effects of hepatocyte growth factor (HGF), which is also referred to as scatter factor (SF). Jiang et al., *Crit. Rev. Oncol. Hematol.* 29: 209–248 (1999). c-Met and HGF are expressed in numerous tissues, although their expression is normally confined predominantly to cells of epithelial and mesenchymal origin, respectively. c-Met and HGF are required for normal mammalian development and have been shown to be important in cell migration, cell proliferation and survival, morphogenic differentiation, and organization of 3-dimensional tubular structures (e.g., renal tubular cells, gland formation, etc.). It is proposed that c-Met-dependent tumor growth, invasion, and dissemination is mediated by these cellular actions. In addition to its effects on epithelial cells, HGF/SF has been reported to be an angiogenic factor, and c-Met signaling in endothelial cells can induce many of the cellular responses necessary for angiogenesis (proliferation, motility, invasion).

The c-Met receptor has been shown to be expressed in a number of human cancers. c-Met and its ligand, HGF, have also been shown to be co-expressed at elevated levels in a variety of human cancers (particularly sarcomas). However, because the receptor and ligand are usually expressed by different cell types, c-Met signaling is most commonly regulated by tumor-stroma (tumor-host) interactions. Furthermore, c-Met gene amplification, mutation, and rearrangement have been observed in a subset of human cancers. Families with germline mutations that activate c-Met kinase are prone to multiple kidney tumors as well as tumors in other tissues. Numerous studies have correlated the expression of c-Met and/or HGF/SF with the state of disease progression of different types of cancer (including lung, colon, breast, prostate, liver, pancreas, brain, kidney, ovaries, stomach, skin, and bone cancers). Furthermore, the overexpression of c-Met or HGF have been shown to correlate with poor prognosis and disease outcome in a number of major human cancers including lung, liver, gastric, and breast. The strong correlation of c-Met with the biology of metastasis and invasion and disease pathogenesis comprises a novel mechanism for treatment of metastatic cancers.

c-Met has been directly implicated in cancers without a successful treatment regimen such as pancreatic cancer, glioma, and hepatocellular carcinoma. A c-Met kinase inhibitor could fill an unmet medical need in the treatment of these cancers.

These observations suggest that c-Met kinase inhibitors would be an effective treatment for primary tumors that are driven by c-Met, but more importantly, would prevent disseminated micrometastases from growing into life-threatening metastases. Therefore, the utility of a c-Met inhibitor extends to preventative and adjuvant therapy settings. In addition, certain cancers (e.g., papillary renal cell carcinoma, some gastric and lung cancers) can be treated which are believed to be driven by c-Met mutation/genetic alteration and dependent on c-Met for growth and survival. These cancers are expected to be sensitive to treatment.

Various human cancers are the primary target indication for c-Met antagonists. These cancers include major cancers such as breast, lung, colorectal, prostate; as well as pancreatic cancer, glioma, liver cancer, gastric cancer, head and neck cancers, melanoma, renal cancer, leukemias, myeloma, and sarcomas.

The compounds presented herein are exemplary only and are not to be construed as limiting the scope of this invention in any manner.

In one aspect, this invention is directed to a pharmaceutical composition comprising one or more compounds of Formula (I) and (II) or a pharmaceutically acceptable salt thereof and a pharmaceutically acceptable excipient.

It is also an aspect of this invention that a compound described herein, or its salt, might be combined with other chemotherapeutic agents for the treatment of the diseases and disorders discussed above. For instance, a compound or salt of this invention might be combined with alkylating agents such as fluorouracil (5-FU) alone or in further combination with leukovorin; or other alkylating agents such as, without limitation, other pyrimidine analogs such as UFT, capecitabine, gemcitabine and cytarabine, the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethiophosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma).

Likewise a compound or salt of this invention might be expected to have a beneficial effect in combination with other antimetabolite chemotherapeutic agents such as, without limitation, folic acid analogs, e.g. methotrexate (used in the treatment of acute lymphocytic leukemia, choriocarcinoma, mycosis fungiodes breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias.

A compound or salt of this invention might also be expected to prove efficacious in combination with natural product based chemotherapeutic agents such as, without limitation, the vinca alkaloids, e.g., vinblastin (used in the treatment of breast and testicular cancer), vincristine and vindesine; the epipodophylotoxins, e.g., etoposide and teniposide, both of which are useful in the treatment of testicular cancer and Kaposi's sarcoma; the antibiotic chemotherapeutic agents, e.g., daunorubicin, doxorubicin, epirubicin, mitomycin (used to treat stomach, cervix, colon, breast, bladder and pancreatic cancer), dactinomycin, temozolomide, plicamycin, bleomycin (used in the treatment of skin, esophagus and genitourinary tract cancer); and the enzymatic chemotherapeutic agents such as L-asparaginase.

In addition to the above, a compound or salt of this invention might be expected to have a beneficial effect used in combination with the platinum coordination complexes (cisplatin, etc.); substituted ureas such as hydroxyurea; methylhydrazine derivatives, e.g., procarbazine; adrenocortical suppressants, e.g., mitotane, aminoglutethimide; and hormone and hormone antagonists such as the adrenocorticosteriods (e.g., prednisone), progestins (e.g.; hydroxyprogesterone caproate); estrogens (e.g., diethylstilbesterol); antiestrogens such as tamoxifen; androgens, e.g., testosterone propionate; and aromatase inhibitors (such as anastrozole.

Finally, the combination of a compound of this invention might be expected to be particularly effective in combination with mitoxantrone or paclitaxel for the treatment of solid tumor cancers or leukemias such as, without limitation, acute myelogenous (non-lymphocytic) leukemia.

The above method can be carried out in combination with a chemotherapeutic agent selected from the group consisting of mitotic inhibitors, alkylating agents, antimetabolites, cell cycle inhibitors, enzymes, topoisomerase inhibitors, biological response modifiers, anti-hormones, antiangiogenic agents such as MMP-2, MMP-9 and COX-2 inhibitors, and anti-androgens.

Examples of useful COX-II inhibitors include Vioxx™, CELEBREX™ (alecoxib), valdecoxib, paracoxib, rofecoxib, and Cox 189. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference.

Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13). Some specific examples of MMP inhibitors useful in the present invention are AG-3340, RO 32-3555, RS 13-0830, and the compounds recited in the following list:

3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo[3.2.1]octane-3-carboxylic acid hydroxyamide; (2R, 3R) 1-[4-(2-chloro-4-fluoro-benzyloxy)-benzenesulfonyl]-3-hydroxy-3-methyl-piperidine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; (R) 3-[4-(4-chloro-phenoxy)-benzenesulfonylamino]-tetrahydro-pyran-3-carboxylic acid hydroxyamide; (2R, 3R) 1-[4-(4-fluoro-2-methyl-benzyloxy)-benzenesulfonyl]-3-hydroxy-3-methyl-piperidine-2-carboxylic acid hydroxyamide; 3-[[(4-(4-fluoro-phenoxy)-benxenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxa-bicyclo[3.2.1]octane-3-carboxylic acid hydroxyamide; 3-endo-3-[4-(4-fluoro-phenoxy)-benzenesulfonylamino]-8-oxa-bicyclo[3.2.1]octane-3-carboxylic acid hydroxyamide; and (R) 3-[4-(4-fluoro-phenoxy)-benzenesulfonylamino]-tetrahydro-furan-3-carboxylic acid hydroxyamide; and pharmaceutically acceptable salts and solvates of said compounds.

Other anti-angiogenesis agents, including other COX-II inhibitors and other MMP inhibitors, can also be used in the present invention.

Compounds of the Formulae (I) and (II) can also be used with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, for example, HERCEPTIN.™ (Genentech, Inc. of South San Francisco, Calif., USA). EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein.

EGFR-inhibiting agents include, but are not limited to, the monoclonal antibodies C225 and anti-EGFR 22Mab (ImClone Systems Incorporated of New York, N.Y., USA), the compounds ZD-1839 (AstraZeneca), BIBX-1382 (Boehringer Ingelheim), MDX-447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Mass.).

These and other EGFR-inhibiting agents can be used in the present invention.

VEGF inhibitors, for example SU-5416, SU 11248, SU-6668 (Sugen Inc. of South San Francisco, Calif., USA), can also be combined with a compound of the Formulae (I) and (II). VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 01/60814,WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun.26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are incorporated herein in their entireties by reference. Other examples of some specific VEGF inhibitors useful in the present invention are IM862 (Cytran Inc. of Kirkland, Wash., USA); anti-VEGF monoclonal antibody of Genentech, Inc. of South San Francisco, Calif.; and angiozyme, a synthetic ribozyme from Ribozyme (Boulder, Colo.) and Chiron (Emeryville, Calif.). These and other VEGF inhibitors can be used in the present invention as described herein.

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), can furthermore be combined with a compound of the Formula (I) or (II), for example those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are incorporated in their entireties herein by reference. The erbB2 receptor inhibitor compounds and substance described in the aforementioned PCT applications, U.S. patents, and U.S. provisional applications, as well as other compounds and substances that inhibit the erbB2 receptor, can be used with compounds of the Formulae (I) and (II), in accordance with the present invention.

Compounds of the Formula (I) and (II) can also be used with other agents useful in treating cancer, including, but not limited to, agents capable of enhancing antitumor immune responses, such as CTLA4 (cytotoxic lymphocite antigen 4) antibodies, and other agents capable of blocking CTLA4; and anti-proliferative agents such as other farnesyl protein transferase inhibitors, for example the farnesyl protein transferase inhibitors described in the references cited in the "Background" section, of U.S. Pat. No. 6,258,824 B1. Specific CTLA4 antibodies that can be used in the present invention include those described in U.S. Provisional Application 60/113,647 (filed Dec. 23, 1998) which is incorporated by reference in its entirety, however other CTLA4 antibodies can be used in the present invention.

The above method can be also be carried out in combination with radiation therapy, wherein the amount of a compound of the Formula (I) and (II), in combination with the radiation therapy, is effective in treating the above diseases. The level of radiation therapy administered may be reduced to a sub-efficacy dose when administered in combination with the compounds of the preferred embodiments of the present invention.

Techniques for administering radiation therapy are known in the art, and these techniques can be used in the combination therapy described herein. The administration of the compound of the invention in this combination therapy can be determined as described herein.

Another aspect of the invention is directed ot the use of compounds of the Formulae (I) and (II) in the preparation of a medicament, which is useful in the treatment of a disease mediated by abnormal Met kinase activity.

"Pharmaceutically acceptable salt" or "pharmaceutically acceptable salt thereof" refer to those salts which retain the biological effectiveness and properties of the free bases and which are obtained by reaction with inorganic or organic acids, such as hydrochloric acid, hydrobromic acid, hydroiodic acid, sulfuric acid, nitric acid, phosphoric acid, methanesulfonic acid, ethanesulfonic acid, p-toluenesulfonic acid, salicylic acid, acetic acid, benzenesulfonic acid (besylate), benzoic acid, camphorsulfonic acid, citric acid, fumaric acid, gluconic acid, glutamic acid, isethionic acid, lactic acid, maleic acid, malic acid, mandelic acid, mucic acid, pamoic acid, pantothenic acid, succinic acid, tartaric acid, and the like.

A "pharmaceutical composition" refers to a mixture of one or more of the compounds described herein, or physiologically acceptable salts thereof, with other chemical components, such as physiologically acceptable carriers and excipients. The purpose of a pharmaceutical composition is to facilitate administration of a compound to an organism.

As used herein, a "physiologically acceptable carrier" refers to a carrier or diluent that does not cause significant irritation to an organism and does not abrogate the biological activity and properties of the administered compound.

An "excipient" refers to an inert substance added to a pharmaceutical composition to further facilitate administration of a compound. Examples, without limitation, of excipients include calcium carbonate, calcium phosphate, various sugars and types of starch, cellulose derivatives (including microcrystalline cellulose), gelatin, vegetable oils, polyethylene glycols, diluents, granulating agents, lubricants, binders, disintegrating agents, and the like.

"Alkyl" refers to a saturated aliphatic hydrocarbon including straight chain, branched chain or cyclic groups. Preferably, the alkyl group has 1 to 20 carbon atoms (whenever a numerical range; e.g., "1–20", is stated herein, it means that the group, in this case the alkyl group, may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, each substituent group is preferably one or more individually selected from halogen, -hydroxy, —COR', —COOR', OCOR', —CONRR', —RNCOR', —NRR', —CN, —NO$_2$, —CZ$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. R and R' are independently H, alkyl, or aryl, wherein alkyl or aryl may be further substituted with halogen, $(CH_2)_nN(R'')_2$, $(CH_2)_nCO_2R''$, $(CH_2)_nOR''$, $(CH_2)_n$OC(O)R', alkoxycarbonyl, aryloxycarbonyl, aminocarbonyl, a heteroalicyclic ring, aryl, alkoxy, —OCZ$_3$, aryloxy, C(O)NH$_2$ or heteroaryl. R" is H, alkyl or aryl, n is 0–3.

"Alkenyl" refers to an aliphatic hydrocarbon having at least one carbon-carbon double bond, including straight chain, branched chain or cyclic groups having at least one carbon-carbon double bond. Preferably, the alkenyl group has 2 to 20 carbon atoms (whenever a numerical range; e.g., "2–20", is stated herein, it means that the group, in this case the alkenyl group, may contain 2 carbon atoms, 3 carbon atoms, etc. up to and including 20 carbon atoms). More preferably, it is a medium size alkenyl having 2 to 10 carbon atoms. Most preferably, it is a lower alkenyl having 2 to 6 carbon atoms. The alkenyl group may be substituted or unsubstituted. When substituted, each substituent group is preferably one or more individually selected from halogen, -hydroxy, —COR', —COOR', OCOR', —CONRR', —RNCOR', —NRR', —CN, —NO$_2$, —CZ$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. Wherein R and R' are defined herein.

"Alkynyl" refers to an aliphatic hydrocarbon having at least one carbon-carbon triple bond, including straight chain, branched chain or cyclic groups having at least one carbon-carbon triple bond. Preferably, the alkenyl group has 2 to 20 carbon atoms (whenever a numerical range; e.g., "2–20", is stated herein, it means that the group, in this case the alkynyl group, may contain 2 carbon atoms, 3 carbon atoms, etc. up to and including 20 carbon atoms). More preferably, it is a medium size alkynyl having 2 to 10 carbon atoms. Most preferably, it is a lower alkynyl having 2 to 6 carbon atoms. The alkynyl group may be substituted or unsubstituted. When substituted, each substituent group is preferably one or more individually selected from halogen, -hydroxy, —COR', —COOR', OCOR', —CONRR', —RNCOR', —NRR', —CN, —NO$_2$, —CZ$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. Wherein R and R' are defined herein.

A "cycloalkyl" or an "alicyclic" group refers to an all-carbon monocyclic or fused ring (i.e., rings which share an adjacent pair of carbon atoms) group wherein one or more of the rings does not have a completely conjugated pi-electron system. Examples, without limitation, of cycloalkyl groups are cyclopropane, cyclobutane, cyclopentane, cyclopentene, cyclohexane, adamantane, cyclohexadiene, cycloheptane and, cycloheptatriene. A cycloalkyl group may be substituted or unsubstituted. When substituted, each substituent group is preferably one or more individually selected from halogen, -hydroxy, —COR', —COOR', OCOR', —CONRR', —RNCOR', —NRR', —CN, —NO$_2$, —CZ$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. Wherein R and R' are defined herein.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, each substituted group is preferably one or more selected halogen, hydroxy, alkoxy, aryloxy, —COR', —COOR', OCOR', —CONRR', —RNCOR', —NRR', —CN, —NO$_2$, —CZ$_3$, —OCZ$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. Wherein R and R' are defined herein.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Examples, without limitation, of heteroaryl groups are pyrrole, furan, thiophene, imidazole, oxazole, thiazole, pyrazole, pyridine, pyrimidine, quinoline, isoquinoline, purine and carbazole. The heteroaryl group may be substituted or unsubstituted. When substituted, each substituted group is preferably one or more selected from halogen, -hydroxy, —COR', —COOR', OCOR', —CONRR', —RNCOR', —NRR', —CN, —NO$_2$, —CZ$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl, where Z is halogen. Wherein R and R' are defined herein.

A "heteroalicyclic ring" or "heteroalicycle" group refers to a monocyclic or fused ring group having in the ring(s) one or more atoms selected from the group consisting of nitrogen, oxygen and sulfur. The rings may also have one or more double bonds. However, the rings may not have a completely conjugated pi-electron system. The heteroalicyclic ring may be substituted or unsubstituted. The heteroalicyclic ring may contain one or more oxo groups. When substituted, the substituted group(s) is preferably one or more selected halogen, hydroxy, —COR', —COOR', OCOR', —CONRR', —RNCOR', —NRR', —CN, —NO$_2$, —CZ$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. Wherein R and R' are defined herein.

Z refers to a halogen group selected from the group consisting of fluorine, chlorine, bromine and iodine.

A "hydroxy" group refers to an —OH group.

An "alkoxy" group refers to both an —O-alkyl and an —O-cycloalkyl group, as defined herein.

An "alkoxycarbonyl" refers to a —C(O)—OR.

An "aminocarbonyl" refers to a —C(O)—NRR'.

An "aryloxycarbonyl" refers to —C(O)—Oaryl.

An "aryloxy" group refers to both an —O-aryl and an —O-heteroaryl group, as defined herein.

An "arylalkyl" group refers to -alkyl-aryl, where alkyl and aryl are defined herein.

An "arylsulfonyl" group refers to a —SO$_2$-aryl.

An "alkylsulfonyl" group refer to a —SO$_2$-alkyl.

A "heteroaryloxyl" group refers to a heteroaryl-O— group with heteroaryl as defined herein.

A "heteroalicycloxy" group refers to a heteroalicyclic-O— group with heteroalicyclic as defined herein.

A "carbonyl" group refers to a —C(=O)—R.

An "aldehyde" group refers to a carbonyl group where R is hydrogen.

A "thiocarbonyl" group refers to a —C(=S)—R group.

A "trihalomethanecarbonyl" group refers to a Z$_3$C—C(O)— group.

A "C-carboxyl" group refers to a —C(O)O—R groups.

An "O-carboxyl" group refers to a R—C(O)O— group.

A "carboxylic acid" group refers to a C-carboxyl group in which R is hydrogen.

A "halo" or "halogen" group refers to fluorine, chlorine, bromine or iodine.

A "trihalomethyl" group refers to a —CZ$_3$ group.

A "trihalomethanesulfonyl" group refers to a Z$_3$CS(O)$_2$ group.

A "trihalomethanesulfonamido" group refers to a Z$_3$CS(O)$_2$NR— group.

A "sulfinyl" group refers to a —S(O)—R group.

A "sulfonyl" group refers to a —S(O)$_2$R group.

An "S-sulfonamido" group refers to a —S(O)$_2$NRR' group.

An "N-Sulfonamido" group refers to a —NR—S(O)$_2$ R group.

An "O-carbamyl" group refers to a —OC(O)NRR' group.

An "N-carbamyl" group refers to a ROC(O)NR— group.

An "O-thiocarbamyl" group refers to a —OC(S)NRR' group.

An "N-thiocarbamyl" group refers to a ROC(S)NR'— group.

An "amino" group refers to an —NH$_2$ or an —NRR' group.

A "C-amido" group refers to a —C(O)NRR' group.

An "N-amido" group refers to a R'C(O)NR— group.

A "nitro" group refers to a —NO$_2$ group.

A "cyano" group refers to a —CN group.

A "silyl" group refers to a —Si(R)$_3$ group.

A "phosphonyl" group refers to a P(=O)(OR)$_2$ group.

An "aminoalkyl" group refers to an -alkylNRR' group.

An "alkylaminoalkyl" group refers to an -alkyl-NR-alkyl group.

A "dialkylamionalkyl" group refers to an -alkyl-N-(alkyl)$_2$ group.

A "perfluoroalkyl group" refers to an alkyl group where all of the hydrogen atoms have been replaced with fluorine atoms.

The definitions of $R_1$–$R_{10}$, G, R, R' and R'' are defined in the present specification.

Compounds that have the same molecular formula but differ in the nature or sequence of bonding of their atoms or arrangements of their atoms in space are termed "isomers." Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". The chemical formulae referred to herein may exhibit the phenomena of tautomerism and structural isomerism. This invention encompasses any tautomeric or structural isomeric form and mixtures thereof which possess the ability to modulate c-Met activity and is not limited to any one tautomeric or structural isomeric form. This invention encompasses any tautomeric or structural isomeric form and mixtures thereof which possess the ability to modulate c-Met activity and is not limited to any one tautomeric or structural isomeric form.

The compounds of this invention may possess one or more asymmetric centers; such compounds can therefore be produced as individual (R)- or (S)-stereoisomers or as mixtures thereof. For example, if the $R_2$ and $R_3$ substituents in a compound of Formula (I) are different, then that carbon is an asymmetric center. Thus, the compound of Formula (I) can exist as an (R)- or (S)-stereoisomer. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992). Thus, this invention also encompasses any stereoisomeric form, their corresponding enantiomers (d- and 1- or (+) and (−) isomers) and diastereomers thereof, and mixtures thereof, which possess the ability to modulate c-Met activity and is not limited to any one stereoisomeric form.

The compounds of the Formulae (I) and (II) may exhibit the phenomena of tautomerism and structural isomerism. For example, the compounds described herein may adopt an E or a Z configuration about a double bond or they may be a mixture of E and Z. This invention encompasses any tautomeric or structural isomeric form and mixtures thereof which possess the ability to modulate c-Met activity and is not limited to any one tautomeric or structural isomeric form.

It is contemplated that compounds of the Formula (I) and (II) would be metabolized by enzymes in the body of the organism such as human being to generate a metabolite that can modulate the activity of c-Met. Such metabolites are within the scope of the present invention.

The term "method" refers to manners, means, techniques and procedures for accomplishing a given task including, but not limited to, those manners, means, techniques and procedures either known to, or readily developed from known manners, means, techniques and procedures by, practitioners of the chemical, pharmaceutical, biological, biochemical and medical arts.

As used herein, the term "modulation" or "modulating" refers to the alteration of the catalytic activity of c-Met. In particular, modulating refers to the activation of the catalytic activity of c-Met, preferably the activation or inhibition of the catalytic activity of c-Met, depending on the concentration of the compound or salt to which c-Met is exposed or, more preferably, the inhibition of the catalytic activity of c-Met.

The term "contacting" as used herein refers to bringing a compound of this invention and c-Met together in such a manner that the compound can affect the catalytic activity of c-Met, either directly, i.e., by interacting with c-Met itself, or indirectly, i.e., by interacting with another molecule on which the catalytic activity of c-Met is dependent. Such "contacting" can be accomplished in vitro, i.e., in a test tube, a petri dish or the like. In a test tube, contacting may involve only a compound and c-Met or it may involve whole cells. Cells may also be maintained or grown in cell culture dishes and contacted with a compound in that environment. In this context, the ability of a particular compound to affect a c-Met related disorder, i.e., the $IC_{50}$ of the compound, defined below, can be determined before use of the compounds in vivo with more complex living organisms is attempted. For cells outside the organism, multiple methods exist, and are well-known to those skilled in the art, to get c-Met in contact with the compounds including, but not limited to, direct cell microinjection and numerous transmembrane carrier techniques.

"In vitro" refers to procedures performed in an artificial environment such as, e.g., without limitation, in a test tube or culture medium. The skilled artisan will understand that, for example, isolated c-Met may be contacted with a modulator in an in vitro environment. Alternatively, an isolated cell may be contacted with a modulator in an in vitro environment.

As used herein, "in vivo" refers to procedures performed within a living organism such as, without limitation, a mouse, rat, rabbit, ungulate, bovine, equine, porcine, canine, feline, primate, or human.

As used herein, "c-Met related disorder," refers to a condition characterized by inappropriate, i.e., under-activity or, more commonly, over-activity of the c-Met catalytic activity. A "c-Met related disorder" also refers to a condition where there may be a mutation in the gene that produces c-Met, which, in turn, produces a c-Met that has an increased or decreased c-Met catalytic activity.

Inappropriate catalytic activity can arise as the result of either: (1) c-Met expression in cells which normally do not express c-Met, (2) increased c-Met expression leading to unwanted cell proliferation, differentiation and/or growth, or, (3) decreased c-Met expression leading to unwanted reductions in cell proliferation, differentiation and/or growth. Over-activity of a c-Met refers to either amplification of the gene encoding a c-Met or production of a level of c-Met activity which can correlate with a cell proliferation, differentiation and/or growth disorder (that is, as the level of the c-Met increases, the severity of one or more of the symptoms of the cellular disorder increases). Under-activity is, of course, the converse, wherein the severity of one or more symptoms of a cellular disorder increase as the level of the c-Met activity decreases.

As used herein, the terms "prevent", "preventing" and "prevention" refer to a method for barring an organism from acquiring a c-Met related disorder in the first place.

As used herein, the terms "treat", "treating" and "treatment" refer to a method of alleviating or abrogating a c-Met mediated cellular disorder and/or its attendant symptoms. With regard particularly to cancer, these terms simply mean that the life expectancy of an individual affected with a cancer will be increased or that one or more of the symptoms of the disease will be reduced.

The term "organism" refers to any living entity comprised of at least one cell. A living organism can be as simple as, for example, a single eukaryotic cell or as complex as a mammal. In a preferred aspect, the organism is a mammal. In a particularly preferred aspect, the mammal is a human being.

The term "therapeutically effective amount" as used herein refers to that amount of the compound being administered which will relieve to some extent one or more of the symptoms of the disorder being treated. In reference to the treatment of cancer, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth, and/or, (4) relieving to some extent (or, preferably, eliminating) one or more symptoms associated with the cancer.

By "monitoring" is meant observing or detecting the effect of contacting a compound with a cell expressing a c-Met. The observed or detected effect can be a change in cell phenotype, in the catalytic activity of c-Met or a change in the interaction of c-Met with a natural binding partner. Techniques for observing or detecting such effects are well-known in the art. For example, the catalytic activity of c-Met may be observed by determining the rate or amount of phosphorylation of a target molecule.

"Cell phenotype" refers to the outward appearance of a cell or tissue or the biological function of the cell or tissue. Examples, without limitation, of a cell phenotype are cell size, cell growth, cell proliferation, cell differentiation, cell survival, apoptosis, and nutrient uptake and use. Such phenotypic characteristics are measurable by techniques well-known in the art.

A "natural binding partner" refers to a polypeptide that binds to a c-Met in a cell. Natural binding partners can play a role in propagating a signal in a c-Met-mediated signal transduction process. A change in the interaction of the natural binding partner with c-Met can manifest itself as an increased or decreased concentration of the c-Met/natural binding partner complex and, as a result, in an observable change in the ability of c-Met to mediate signal transduction.

As used herein, "administer" or "administration" refers to the delivery of a compound or salt of the present invention or of a pharmaceutical composition containing a compound or salt of this invention to an organism for the purpose of prevention or treatment of a c-Met-related disorder.

A "pharmaceutical composition" refers to a mixture of one or more of the compounds described herein, or pharmaceutically acceptable salts or prodrugs thereof, with other chemical components, such as pharmaceutically acceptable excipients. The purpose of a pharmaceutical composition is to facilitate administration of a compound to an organism.

"Pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

"Pharmaceutically acceptable salt" refers to those salts, which retain the biological effectiveness and properties of the parent compound. Such salts include:

(1) acid addition salt which is obtained by reaction of the free base of the parent compound with inorganic acids such as hydrochloric acid, hydrobromic acid, nitric acid, phosphoric acid, sulfuric acid, and perhcloric acid and the like, or with organic acids such as acetic acid, oxalic acid, (D) or (L) malic acid, maleic acid, methanesulfonic acid, ethanesulfonic acid, p-toluenesulfonic acid, salicylic acid, tartaric acid, citric acid, succinic acid or malonic acid and the like, preferably hydrochloric acid or (L)-malic acid; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The compounds of the Formulae (I) and (II) may also act as prodrugs. A "prodrug" refers to an agent, which is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. An example, without limitation, of a prodrug would be a compound of the present invention, which is, administered as an ester (the "prodrug"), carbamate or urea.

Indications

A precise understanding of the mechanism by which the compounds of the invention, in particular, the compounds generated in vivo from the compounds of the invention, inhibit c-Met is not required in order to practice the present invention. However, while not hereby being bound to any particular mechanism or theory, it is believed that the compounds interact with the amino acids in the catalytic region of c-Met. The compounds disclosed herein may thus have utility as in vitro assays for c-Met as well as exhibiting in vivo therapeutic effects through interaction with c-Met.

In another aspect, this invention relates to a method for treating or preventing a c-Met related disorder by administering a therapeutically effective amount of a compound of this invention, or a salt thereof, to an organism.

It is also an aspect of this invention that a pharmaceutical composition containing a compound of this invention, or a salt thereof, is administered to an organism for the purpose of preventing or treating a c-Met related disorder.

This invention is therefore directed to compounds that modulate PK signal transduction by affecting the enzymatic activity of c-Met, thereby interfering with the signal transduced by c-Met. More particularly, the present invention is directed to compounds which modulate c-Met mediated signal transduction pathways as a therapeutic approach to treat the many cancers described herein.

A method for identifying a chemical compound that modulates the catalytic activity of c-Met is another aspect of this invention. The method involves contacting cells expressing c-Met with a compound of this invention (or its salt) and monitoring the cells for any effect that the compound has on them. Alternatively, the method can involve contacting the c-Met protein itself (i.e., not in a cell) with a chemical compound of the preferred embodiments of the present invention and monitoring the protein for any effect that the compound has on it. The effect may be observable, either to the naked eye or through the use of instrumentation. The effect may be, for example, a change or absence in a cell phenotype. The change or absence of change in the cell phenotype monitored, for example, may be, without limitation, a change or absence of change in the catalytic activity of c-Met in the cells or a change or absence of change in the interaction of c-Met with a natural binding partner.

Pharmaceutical Compositions and Use

A compound of the present invention or a physiologically acceptable salt thereof, can be administered as such to a human patient or can be administered in pharmaceutical compositions in which the foregoing materials are mixed with suitable carriers or excipient(s). Techniques for formulation and administration of drugs may be found in "Remington's Pharmacological Sciences," Mack Publishing Co., Easton, Pa., latest edition.

Routes of Administration

Suitable routes of administration may include, without limitation, oral, intraoral, rectal, transmucosal or intestinal administration or intramuscular, epicutaneous, parenteral, subcutaneous, transdermal, intramedullary, intrathecal, direct intraventricular, intravenous, intravitreal, intraperitoneal, intranasal, intramuscular, intradural, intrarespiratory, nasal inhalation or intraocular injections. The preferred routes of administration are oral and parenteral.

Alternatively, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

Composition/Formulation

Pharmaceutical compositions of the present invention may be manufactured by processes well known in the art, e.g., by means of conventional mixing, dissolving, granulating, dragee-making, levigating, emulsifying, encapsulating, entrapping, lyophilizing processes or spray drying.

Pharmaceutical compositions for use in the methods of the present invention may be prepared by any methods of pharmacy, but all methods include the step of bringing in association the active ingredient with the carrier which constitutes one or more necessary ingredients. In particular, pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

Dosage forms include tablets, troches, dispersions, suspensions, solutions, capsules, patches, syrups, elixirs, gels, powders, magmas, lozenges, ointments, creams, pastes, plasters, lotions, discs, suppositories, nasal or oral sprays, aerosols and the like.

For injection, the compounds of the invention may be formulated in aqueous solutions, preferably in physiologically compatible buffers such buffers with or without a low concentration of surfactant or cosolvent, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethylcellulose, sodium carboxymethylcellulose, and/or polyvinyl-pyrrolidone (PVP). If desired, disintegrating agents may be added, such as cross-linked polyvinyl pyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, liquid polyethylene glycols, cremophor, capmul, medium or long chain mono- di- or triglycerides. Stabilizers may be added in these formulations, also.

For administration by inhalation, the compounds for use according to the present invention are conveniently delivered in the form of an aerosol spray using a pressurized pack or a nebulizer and a suitable propellant, e.g., without limitation, dichlorodifluoromethane, trichlorofluoromethane, dichlorotetra-fluoroethane or carbon dioxide. In the case of a pressurized aerosol, the dosage unit may be controlled by providing a valve to deliver a metered amount. Capsules and cartridges of, for example, gelatin for use in an inhaler or insulator may be formulated containing a powder mix of the compound and a suitable powder base such as lactose or starch.

The compounds may also be formulated for parenteral administration, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use.

The compounds may also be formulated in rectal compositions such as suppositories or retention enemas, using, e.g., conventional suppository bases such as cocoa butter or other glycerides.

In addition to the formulations described previously, the compounds may also be formulated as depot preparations. Such long acting formulations may be administered by implantation (for example, subcutaneously or intramuscularly) or by intramuscular injection. A compound of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

A non-limiting example of a pharmaceutical carrier for the hydrophobic compounds of the invention is a cosolvent system comprising benzyl alcohol, a nonpolar surfactant, a water-miscible organic polymer and an aqueous phase such as the VPD co-solvent system. VPD is a solution of 3% w/v benzyl alcohol, 8% w/v of the nonpolar surfactant Polysorbate 80, and 65% w/v polyethylene glycol 300, made up to volume in absolute ethanol. The VPD co-solvent system (VPD:D5W) consists of VPD diluted 1:1 with a 5% dextrose in water solution. This co-solvent system dissolves hydrophobic compounds well, and itself produces low toxicity upon systemic administration. Naturally, the proportions of such a co-solvent system may be varied considerably without destroying its solubility and toxicity characteristics. Furthermore, the identity of the co-solvent components may be varied: for example, other low-toxicity nonpolar surfactants may be used instead of Polysorbate 80, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. In addition, certain organic solvents such as dimethylsulfoxide also may be employed, although often at the cost of greater toxicity.

Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions herein also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Many of the PK modulating compounds of the invention may be provided as physiologically acceptable salts wherein the claimed compound may form the negatively or the positively charged species. Examples of salts in which the compound forms the positively charged moiety include, without limitation, quaternary ammonium (defined elsewhere herein), salts such as the hydrochloride, sulfate, carbonate, lactate, tartrate, maleate, succinate, malate, acetate and methylsulfonate ($CH_3SO_3$), wherein the nitrogen atom of the quaternary ammonium group is a nitrogen of the selected compound of this invention which has reacted with the appropriate acid. Salts in which a compound of this invention forms the negatively charged species include, without limitation, the sodium, potassium, calcium and magnesium salts formed by the reaction of a carboxylic acid group in the compound with an appropriate base (e.g. sodium hydroxide (NaOH), potassium hydroxide (KOH), Calcium hydroxide ($Ca(OH)_2$), etc.).

Dosage

Pharmaceutical compositions suitable for use in the present invention include compositions wherein the active ingredients are contained in an amount sufficient to achieve the intended purpose, i.e., the modulation of PK activity or the treatment or prevention of a PK-related disorder.

More specifically, a therapeutically effective amount means an amount of compound effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any compound used in the methods of the invention, the therapeutically effective amount or dose can be estimated initially from cell culture assays. Then, the dosage can be formulated for use in animal models so as to achieve a circulating concentration range that includes the $IC_{50}$ as determined in cell culture (i.e., the concentration of the test compound which achieves a half-maximal inhibition of c-Met activity). Such information can then be used to more accurately determine useful doses in humans.

Toxicity and therapeutic efficacy of the compounds described herein can be determined by standard pharmaceutical procedures in cell cultures or experimental animals, e.g., by determining the $IC_{50}$ and the $LD_{50}$ (both of which are discussed elsewhere herein) for a subject compound. The data obtained from these cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to provide plasma levels of the active species which are sufficient to maintain the kinase modulating effects. These plasma levels are referred to as minimal effective concentrations (MECs). The MEC will vary for each compound but can be estimated from in vitro data, e.g., the concentration necessary to achieve 50–90% inhibition of a kinase may be ascertained using the assays described herein. Dosages necessary to achieve the MEC will depend on individual characteristics and route of administration. HPLC assays or bioassays can be used to determine plasma concentrations.

Dosage intervals can also be determined using MEC value. Compounds should be administered using a regimen that maintains plasma levels above the MEC for 10–90% of the time, preferably between 30–90% and most preferably between 50–90%. At present, the therapeutically effective amounts of compounds of the Formulae (I) and (II) may range from approximately 10 mg/m² to 1000 mg/m² perday. Even more preferably 25 mg/m² to 500 mg/m².

In cases of local administration or selective uptake, the effective local concentration of the drug may not be related to plasma concentration and other procedures known in the art may be employed to determine the correct dosage amount and interval.

The amount of a composition administered will, of course, be dependent on the subject being treated, the severity of the affliction, the manner of administration, the judgment of the prescribing physician, etc.

Packaging

The compositions may, if desired, be presented in a pack or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, and the like.

EXAMPLES

Experimental Part:

Scheme I. General Synthetic Procedure

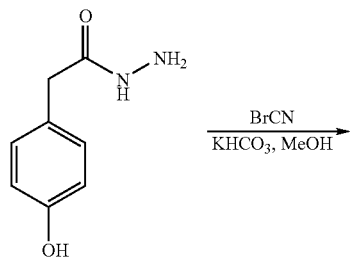

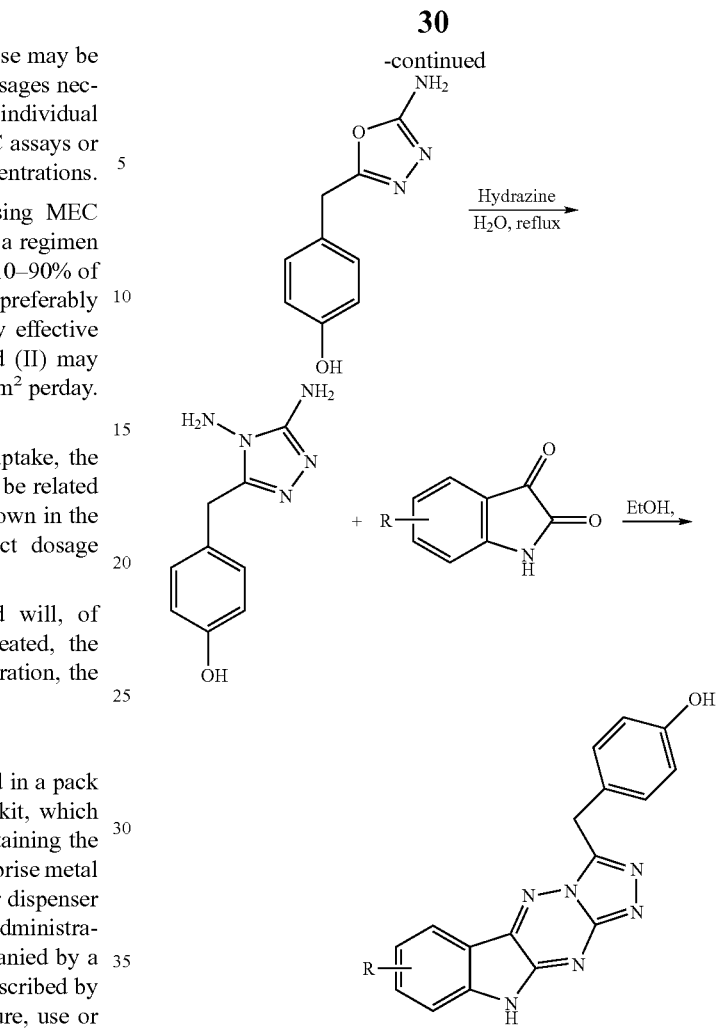

Example 1

(4-Hydroxy-phenyl)-acetic acid hydrazide

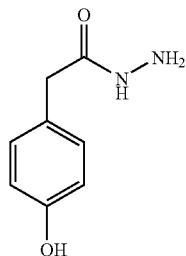

Neat anhydrous hydrazine 21.0 g (654 mmol) was added to a solution of p-hydroxyphenylacetic acid methyl ester 27.18 g (163.5 mmol) in MeOH (100 mL) and the mixture was heated to 50–55° C. and stirred at this temperature for 90 min (water bath). Cooled, stirred for extra 1 hour, the precipitate collected by filtration, compressed on the frit, washed with MeOH (3×10 mL) and dried on high vacuum. A second fraction was obtained by cooling the supernatants to −15° C. overnight and filtering the formed precipitate.

Combined yield: 25.13 g of a white crystalline solid (92.5%)

$^1$H-NMR(DMSO-$d_6$, 400 MHz): δ 9.182 (br s, 1H), 9.108 (br s, 1H), 7.035 (app d, J=8.6 Hz, 2H), 6.666 (app d, J=8.6

Hz, 2H), 4.176 (br d, J=3.1 Hz, 2H), 3.207 (s, 2H); $^{13}$C-NMR (DMSO-d$_6$, 100 MHz): 170.66, 156.45, 130,47 (2C), 127.00, 115.63 (2C), 40.48.

Example 2

4-(5-Amino-[1,3,4]oxadiazol-2-ylmethyl)-phenol

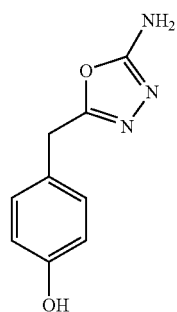

Solid BrCN 6.059 g (57.2 mmol) was added in one portion into ice-cooled slurry of (4-hydroxy-phenyl)-acetic acid hydrazide 8.642 g (52.0 mmol) and KHCO$_3$ 6.510 g (65 mmol) in MeOH (100 mL). The mixture was stirred at 0–5° C. for 1 hour, the ice bath allowed to melt and stirred at room temperature overnight (18 hr). The reaction mixture was diluted with water (100 mL), stirred for 1 hour, the precipitate was collected by filtration, washed with water and dried on high vacuum. A second fraction precipitated after concentrating and cooling the supernatants.

Combined yield: 9.018 g (90.5%) of a white crystalline solid.

$^1$H-NMR(DMSO-d$_6$, 400 MHz): δ 9.334 (s, 1H), 7.040 (app d, J=9.0 Hz, 2H), 6.839 (br s, 2H), 6.706 (app d, J=8.6 Hz, 2H), 3.879 (s, 2H).

Example 3

4-(4,5-Diamino-4H-[1,2,4]triazol-3-ylmethyl)-phenol

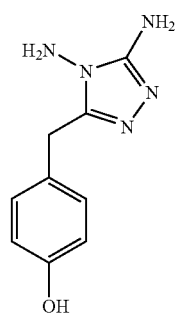

A mixture of 4-(5-amino-[1,3,4]oxadiazol-2-ylmethyl)-phenol 4.902 g (25.64 mmol), water 40 mL and anhydrous hydrazine 13 mL was refluxed on an oil bath (190° C.) for 18 hours. The mixture was cooled, allowed to crystallize at room temperature for 2 hours, then placed into a freezer (−20° C.) overnight (16 hrs). The precipitated product was collected by filtration, washed with chilled MeOH (−15° C.) and dried on high vacuum. The crude product was re-crystallized from water (80 mL, reflux to +4° C. overnight). Filtered, washed with ice-cold water and dried on high vacuum.

Y=1.658 g (31.5%) of a white crystalline solid.
MS+cAPCI: 206(M+1).
MS−cAPCI: 204,202(M−1).
$^1$H-NMR(DMSO-d$_6$, 400 MHz): δ 9.234 (br s, 1H), 7.034 (app d, J=8.6 Hz, 2H), 2H), 6.664 (app d, J=8.6 Hz, 2H), 5.453 (br s, 2H), 5.338 (s, 2H), 3.772 (s, 2H).

Example 4

(4-Fluoro-phenyl)-acetic acid hydrazide

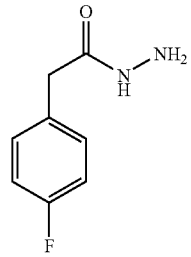

Neat anhydrous hydrazine 20 mL was added to a slurry of (4-fluorophenyl)acetic acid methyl ester (Acros Organics USA, Morris Plains, N.J., 25.66 g, 152.5 mmol) in MeOH (120 mL) and the mixture was heated to 60° C. with reflux condenser under nitrogen for 2 hrs. Cooled to room temperature, evaporated to dryness (room temperature to 60° C., 100 Torr to 7 Torr). The solid residue was re-crystallized from 1-propanol, 100 mL (reflux to room temperature, overnight). The crystallized product was collected by filtration, washed with 1-propanol and dried on high vacuum. [1$^{st}$ fraction]

Evaporating the supernatants to dryness on high vacuum, the obtained solid residue was dried on high vacuum overnight. The residue was then re-crystallized from benzene. (reflux to room temperature, overnight) The precipitated product was collected by filtration, washed with a mixture benzene-hexane (1:1), then with hexane. Dried on high vacuum. [2$^{nd}$ fraction]

Combined yield: 24.855 g of a white crystalline flakes (97%)

$^1$H-NMR(DMSO-d$_6$, 400 MHz): δ 9.194 (br s, 1H), 7.272 (m, 2H), 7.107 (m, 2H), 4.202 (br d, J=4.3 Hz, 2H), 3.329 (s, 2H); $^{19}$F-NMR(DMSO-d$_6$, 376.5 MHz): δ-116.96 (m, 1F).

Example 5

5-(4-Fluoro-benzyl)-[1,3,4]oxadiazol-2-ylamine

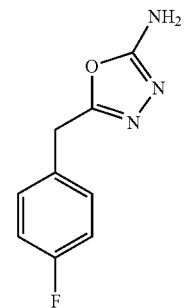

Solid BrCN 13.37 g (130 mmol, 1.1 eq.) was added in one portion into ice-cooled slurry of (4-Fluoro-phenyl)-acetic acid hydrazide (19.85 g, 118 mmol) and KHCO3 14.77 g (147.5 mmol, 1.25 eq.) in MeOH (150 mL) in a 1L flask. (Followed by MeOH 10 mL to wash the funnel). The mixture was stirred on ice bath at 0–5° C. for 2 hours in a loose-capped flask, then the bath allowed to melt gradually and then the mixture was stirred at 5 to 20° C. overnight (17 hrs). The reaction mixture was diluted with water (200 mL), stirred for 1 hour in an open flask, then cooled on ice bath. The precipitate was collected by filtration, washed with water and dried on highvac. [1$^{st}$ fraction]The supernatants were concentrated on rotavap form warm (40° C.) water bath to remove all MeOH and some water. The obtained slurry was cooled to room temperature, the precipitate was collected by filtration, washed with water and dried on highvac. [2$^{nd}$ fraction]. Combined yield: 20.836 g (91.5%) of a white crystalline solid.

$^1$H-NMR(DMSO-d$_6$, 400 MHz): δ 7.289 (m, 2H), 7.148 (m, 2H), 6.873 (br s, 2H), 4.014 (s, 2H); $^{19}$F-NMR(DMSO-d$_6$, 376.5 MHz): δ-116.01 (m, 1F).

Example 6

5-(4-Fluoro-benzyl)-[1,2,4]triazole-3,4-diamine

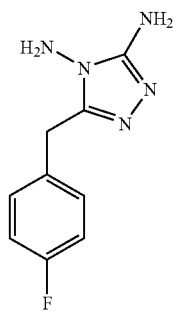

A mixture of 5-(4-fluoro-benzyl)-[1,3,4]oxadiazol-2-ylamine 10.182 g (52.7 mmol), water 80 mL and anhydrous hydrazine 20 mL was refluxed under nitrogen on an oil bath (190–200° C.) for 23 hours. The mixture was cooled and allowed to crystallize at room temperature under nitrogen overnight. The precipitated product was collected by filtration, washed with ice-cold water (10 mL) and dried on high vacuum. The crude product was re-crystallized from water 60 mL (reflux under nitrogen, than to +4° C. in a refrigerator overnight). The product was filtered, washed with ice-cold water and dried on high vacuum.

Y=6.210 g (56.5%) of a large white crystals.

$^1$H-NMR(DMSO-d$_6$, 400 MHz): δ 7.267 (app d, J=8.6 Hz, J=5.5 Hz, 2H), 7.097 (app t, J=9.0 Hz, 2H), 5.509 (br s, 2H), 5.339 (s, 2H), 3.884 (s, 2H); $^{19}$F-NMR(DMSO-d$_6$, 376.5 MHz): δ-117.14 (m, 1F).

Example 7

3,3,4-Trichloro-5-methoxy-1,3-dihydro-indol-2-one

According to the procedure published by R. J. Bass in Tetrahedron 27, 3263–70 (1971), the chlorination of 5-methoxyindole-2-carboxylic acid provided 3,3,4-trichloro-5-methoxy-1,3-dihydro-indol-2-one in 47% Y (after re-crystallization). $^1$H-NMR(CDCl$_3$, 400 MHz): δ 11.342 (br s, 1H), 7.207 (d, J=9.0 Hz, 1H), 6.903 (d, J=8.6 Hz, 1H), 3.846 (s, 3H).

Example 8

4-Chloro-5-methoxy-1H-indole-2,3-dione

Hydrolysis of 3,3,4-trichloro-5-methoxy-1,3-dihydro-indol-2-one in MeOH-water mixture according to the procedure published in Tetrahedron 27, 3263–70 (1971) provided 4-chloro-5-methoxy-1H-indole-2,3-dione as a deep-brown shiny crystals in 96% Y.

$^1$H-NMR(DMSO-d$_6$, 400 MHz): δ 10.996 (br s, 1H), 7.338 (d, J=8.6 Hz, 1H), 6.791 (d, J=8.6 Hz, 1H), 3.825 (s, 3H).

Example 9

3,3,4,7-Tetrachloro-5-methoxy-1,3-dihydro-indol-2-one

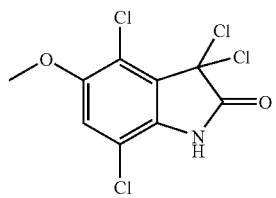

11.54 g of 3,3,4-trichloro-5-methoxy-1,3-dihydro-indol-2-one (43.3 mmol) was suspended in glacial AcOH (200 mL). 3.343 g (21.7 mmol) of N,N-dichlorourethane was added and the mixture was stirred at 60° C. for 2 days. The reaction mixture was cooled to room temperature, the precipitate collected by filtration and dried on high vacuum. Re-crystallization from benzene (150 mL) yielded 6.135 g of product (containing 5% of the start. material as an impurity).

The AcOH-supernatants from the react mixture were diluted with water (200 mL) and the precipitated second fraction was collected by filtration, dried on high vacuum. This second fraction was combined with evap. residue of the benzene supernatants from the first fraction re-crystallization and re-crystallized twice from benzene (2×100 mL). This re-crystallized material (2.300 g) contained 8% of the starting material as an impurity.

Combined yield: 8.521 g (65.5%) of a white crystalline solid.

$^1$H-NMR(DMSO-d$_6$, 400 MHz): δ 11.842 (br s, 1H), 7.370 (s, 1H), 3.879 (s, 3H).

Example 10

4,7-Dichloro-5-methoxy-1H-indole-2,3-dione

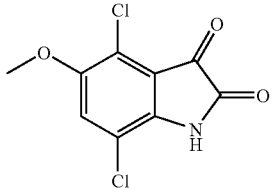

3.841 g of 3,3,4,7-tetrachloro-5-methoxy-1,3-dihydro-indol-2-one (12.76 mmol) was refluxed in a mixture of MeOH (125 mL) and water (75 mL) for 32 hours. Allowed to crystallize overnight, the precipitated product collected by filtration and dried on highvac.

Y=2.708 g of a deep red-brown shiny crystalline solid (86%)

The product contained 3% of 4-Chloro-5-methoxyisatin, originating from the impurity in the starting material.

$^1$H-NMR(DMSO-$d_6$, 400 MHz): δ 11.407 (br s, 1H), 7.447 (s, 1H), 3.857 (s, 3H).

Example 11

4-Chloro-5-hydroxy-1H-indole-2,3-dione

4-Chloro-5-hydroxy-1H-indole-2,3-dione 2.116 g (10 mmol) was suspended in anhydrous dichloromethane (20 mL) and cooled on ice bath under nitrogen. Boron tribromide 3.00 mL (31.7 mmol) was added neat (over 10 minutes) and the obtained mixture was stirred at 0° C. to room temperature for 30 minutes and at room temperature overnight (16 hr) under nitrogen. With cooling on ice bath, the reaction mixture was quenched by slow addition of crushed ice, the mixture was then diluted with methanol (80 mL) and water (150 mL) and stirred for 15 minutes. The precipitate was collected by filtration, washed with mixture of methanol+water (1:2) and dried on high vacuum.

Y=1.716 g (87%) of a brown solid.

$^1$H-NMR(DMSO-$d_6$, 400 MHz): δ 10.877 (br s, 1H), 10.100 (br s, 1H), 7.150 ($d_{AB}$, J=8.6 Hz, 1H), 6.698 ($d_{AB}$, J=8.6 Hz, 1H).

Example 12

Synthesis of 4-Chloro-2,3-dioxo-2,3-dihydro-1H-indole-5-carboxylic acid (two steps)

2-Chloro-4-(2-hydroxyimino-acetylamino)-benzoic acid

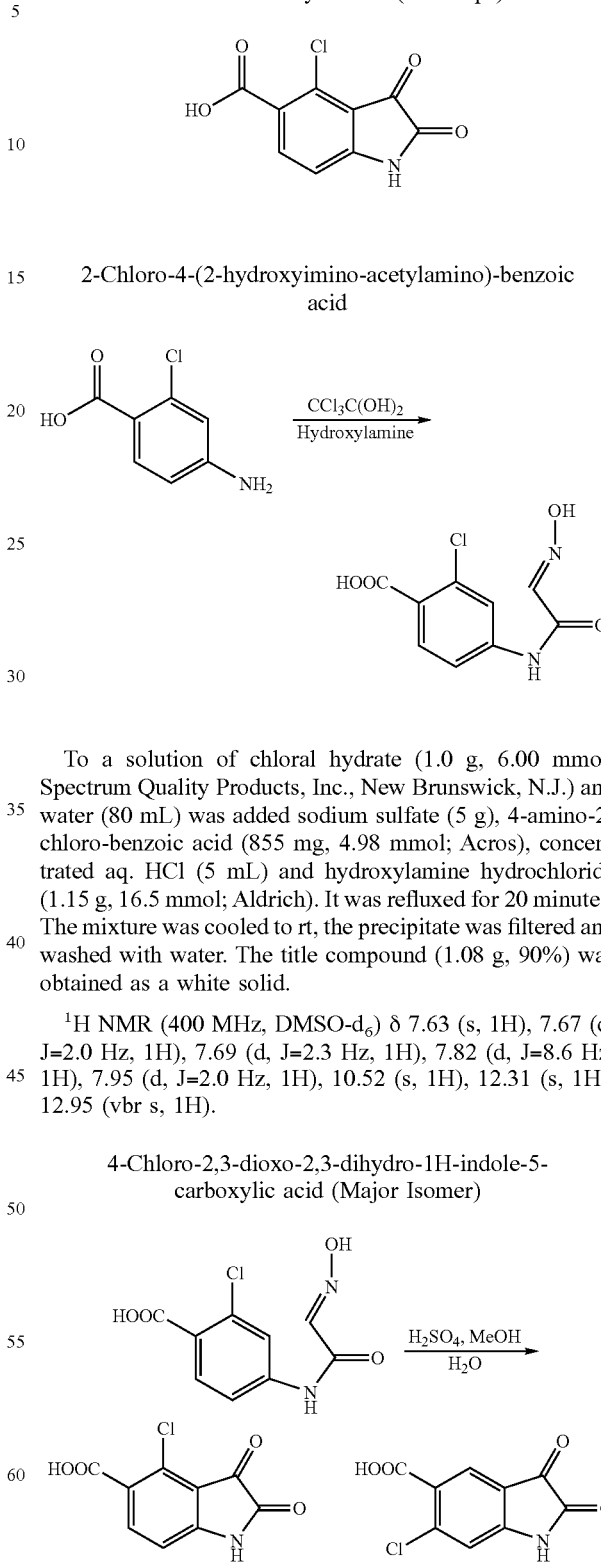

To a solution of chloral hydrate (1.0 g, 6.00 mmol; Spectrum Quality Products, Inc., New Brunswick, N.J.) and water (80 mL) was added sodium sulfate (5 g), 4-amino-2-chloro-benzoic acid (855 mg, 4.98 mmol; Acros), concentrated aq. HCl (5 mL) and hydroxylamine hydrochloride (1.15 g, 16.5 mmol; Aldrich). It was refluxed for 20 minutes. The mixture was cooled to rt, the precipitate was filtered and washed with water. The title compound (1.08 g, 90%) was obtained as a white solid.

$^1$H NMR (400 MHz, DMSO-$d_6$) δ 7.63 (s, 1H), 7.67 (d, J=2.0 Hz, 1H), 7.69 (d, J=2.3 Hz, 1H), 7.82 (d, J=8.6 Hz, 1H), 7.95 (d, J=2.0 Hz, 1H), 10.52 (s, 1H), 12.31 (s, 1H), 12.95 (vbr s, 1H).

4-Chloro-2,3-dioxo-2,3-dihydro-1H-indole-5-carboxylic acid (Major Isomer)

2-chloro-4-[(-2-(hydroxyimino)ethanoyl)amino]benzoic acid (300 mg, 1.24 mmol) was dissolved in concentrated sulfuric acid (5 mL). It was stirred at 80° C. for 3 h. The reaction mixture was cooled to rt, poured into ice water and it was extracted twice with ethylacetate. The title compound was obtained as an orange solid (256 mg, 92%) containing 12% of the regioisomer (6-chloro-2,3-dioxoindoline-5-carboxylic acid).

$^1$H NMR (400 MHz, d$_6$-DMSO) δ 6.88 (d, J=8.6 Hz, 1H), 8.02 (d, J=8.2 Hz, 1H), 11.41 (s, 1H), 13.24 (br s, 1H).

Example 13

4,7-Dimethyl-5-(2-morpholin-4-yl-ethoxy)-1H-indole-2,3-dione

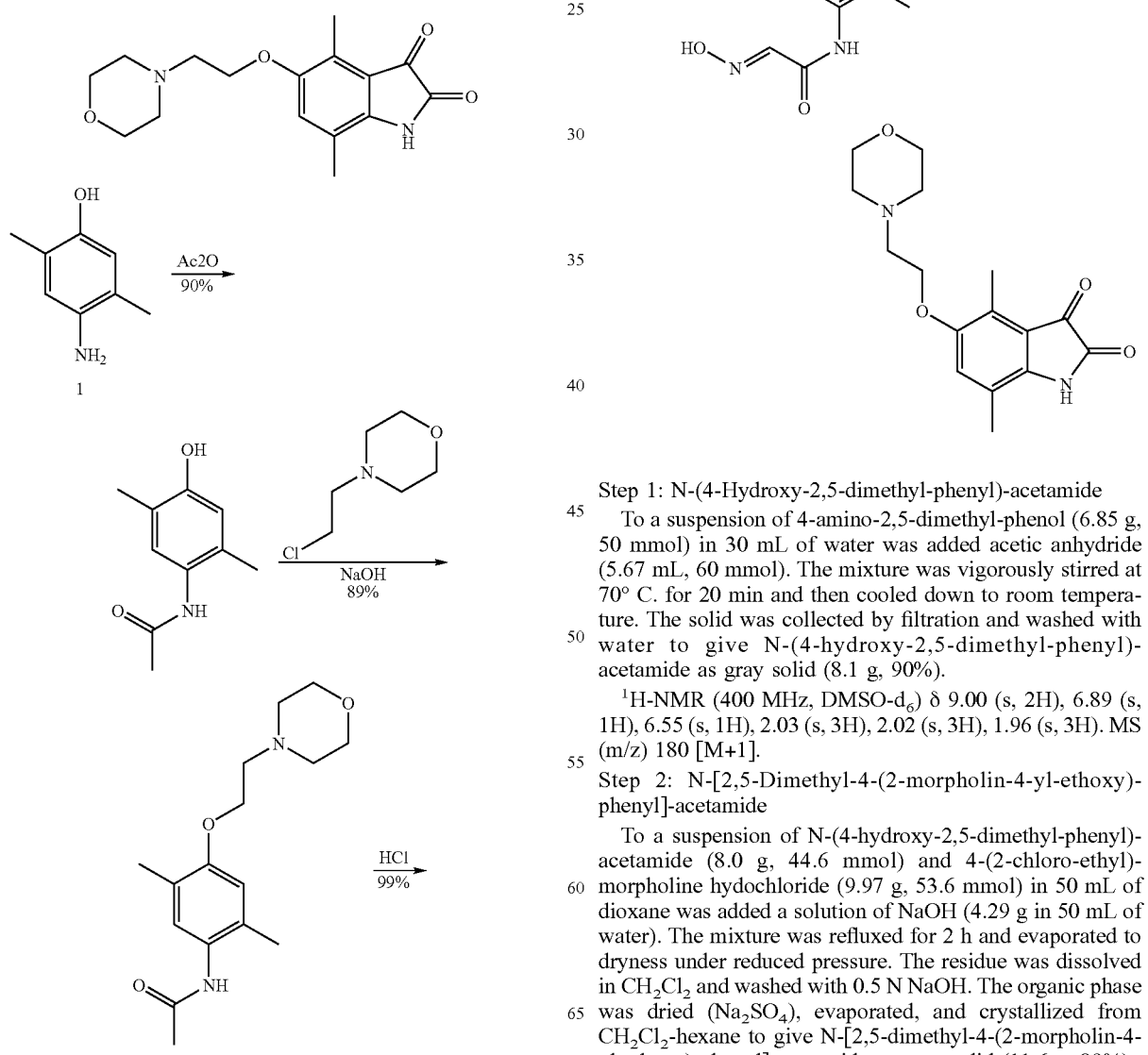

Step 1: N-(4-Hydroxy-2,5-dimethyl-phenyl)-acetamide

To a suspension of 4-amino-2,5-dimethyl-phenol (6.85 g, 50 mmol) in 30 mL of water was added acetic anhydride (5.67 mL, 60 mmol). The mixture was vigorously stirred at 70° C. for 20 min and then cooled down to room temperature. The solid was collected by filtration and washed with water to give N-(4-hydroxy-2,5-dimethyl-phenyl)-acetamide as gray solid (8.1 g, 90%).

$^1$H-NMR (400 MHz, DMSO-d$_6$) δ 9.00 (s, 2H), 6.89 (s, 1H), 6.55 (s, 1H), 2.03 (s, 3H), 2.02 (s, 3H), 1.96 (s, 3H). MS (m/z) 180 [M+1].

Step 2: N-[2,5-Dimethyl-4-(2-morpholin-4-yl-ethoxy)-phenyl]-acetamide

To a suspension of N-(4-hydroxy-2,5-dimethyl-phenyl)-acetamide (8.0 g, 44.6 mmol) and 4-(2-chloro-ethyl)-morpholine hydochloride (9.97 g, 53.6 mmol) in 50 mL of dioxane was added a solution of NaOH (4.29 g in 50 mL of water). The mixture was refluxed for 2 h and evaporated to dryness under reduced pressure. The residue was dissolved in CH$_2$Cl$_2$ and washed with 0.5 N NaOH. The organic phase was dried (Na$_2$SO$_4$), evaporated, and crystallized from CH$_2$Cl$_2$-hexane to give N-[2,5-dimethyl-4-(2-morpholin-4-yl-ethoxy)-phenyl]-acetamide as gray solid (11.6 g, 89%).

$^1$H-NMR (400 MHz, DMSO-d$_6$) δ 9.08 (s, 1H), 7.00(s, 1H), 6.75 (s, 1H), 4.04 (t, 2H), 3.56 (t, 4H), 2.69 (t, 2H), 2.49 (m, 4H), 2.10 (s, 3H), 2.06 (s, 3H), 1.98 (s, 3H). MS (m/z) 293 [M+1].

Step 3: 2,5-Dimethyl-4-(2-morpholin-4-yl-ethoxy)-phenylamine hydrogen chloride

The mixture of N-[2,5-dimethyl-4-(2-morpholin-4-yl-ethoxy)-phenyl]-acetamide (11.4 g, 39 mmol) in 3N aq.HCl (100 mL) was refluxed for 2 h and then concentrated under reduced pressure. The residue was lyophilized to give 2,5-dimethyl-4-(2-morpholin-4-yl-ethoxy)aniline dihydrochloride as gray solid quantitatively.

$^1$H-NMR (400 MHz, DMSO-d$_6$) δ 11.75 (brs, 1H), 10.17 (brs, 3H), 7.22 (s, 1H), 6.94 (s, 1H), 4.45 (t, 2H), 3.77–4.04 (m, 6H), 3.54 (t, 2H), 3.45 (m, 2H), 3.21 (m, 2H), 2.33 (s, 3H), 2.15 (s, 3H). MS (m/z) 251 [M+1].

Step 4: N-[2,5-Dimethyl-4-(2-morpholin-4-yl-ethoxy)-phenyl]-2-hydroxyimino-acetamide To a solution of chloral hydrate (910 mg, 5.5 mmol) in 12 mL of water were added, in order: 13 g of anhydrous Na$_2$SO$_4$; a solution of 2,5-dimethyl-4-(2-morpholin-4-yl-ethoxy)-pheylamine hydrogen chloride (1.61 g, 5 mmol) in water (3 mL); and finally, a solution of hydroxylamine hydrochloride (1.12 g, 16 mmol) in 5 mL of water. The mixture was heated in an oil bath (130° C.) with stirring for 15 min, then cooled down to room temperature, diluted with water, neutralized to pH 7 with concentrate aq. NaHCO$_3$, and extracted with EtOAc. The combined organic layer was was washed with water, dried (Na$_2$SO$_4$) and concentrated under reduced pressure to give N-[2,5-dimethyl-4-(2-morpholin-4-yl-ethoxy)-phenyl]-2-hydroxyimino-acetamide as yellow solid (1.45 g, 91%).

$^1$H-NMR (400 MHz, DMSO-d$_6$) δ 12.04 (s, 1H), 9.34 (s, 1H), 7.60(s, 1H), 7.09 (s, 1H), 6.80 (s, 1H), 4.06 (t, 2H), 3.57 (t, 2H), 2.70 (t, 2H), 2.49 (m, 4H), 2.13 (s, 3H), 2.08 (s, 3H). MS (m/z) 322 [M+1].

Step 5: 4,7-Dimethyl-5-(2-morpholin-4-yl-ethoxy)-1H-indole-2,3-dione

To concentrated H$_2$SO$_4$ (3.5 mL) at 60° C. was added N-[2,5-dimethyl-4-(2-morpholin-4-yl-ethoxy)-phenyl]-2-hydroxyimino-acetamide (1.4 g, 4.36 mmol) in portions with stirring. After the addition was finished, the mixture was heated to 75° C. and kept at this temperature for 15 min. A dark-purple solution was formed and poured upon cracked ice. Then solid NaHCO$_3$ is added and pH was adjusted to 8.0. The mixture was extracted with CH$_2$Cl$_2$, dried (Na$_2$SO$_4$), and crystallized from CH$_2$Cl$_2$-hexane to give 4,7-Dimethyl-5-(2-morpholin-4-yl-ethoxy)-1H-indole-2,3-dione as brown solid 1.15 g, 87%).

$^1$H-NMR (400 MHz, DMSO-d$_6$) δ 10.84 (s, 1H), 7.03 (s, 1H), 4.03 (t, 2H), 3.57 (t, 2H), 2.67 (t, 2H), 2.46 (t, 4H), 2.29 (s, 3H), 2.13 (s, 3H). MS (m/z) 305 [M+1].

Example 14

5-(2-Diethylamino-ethyl)-4,7-dimethyl-1H-indole-2,3-dione hydrochloride

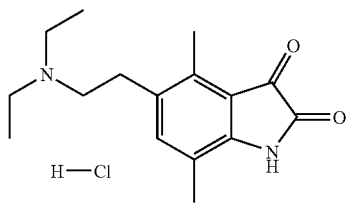

Synthetic Scheme:

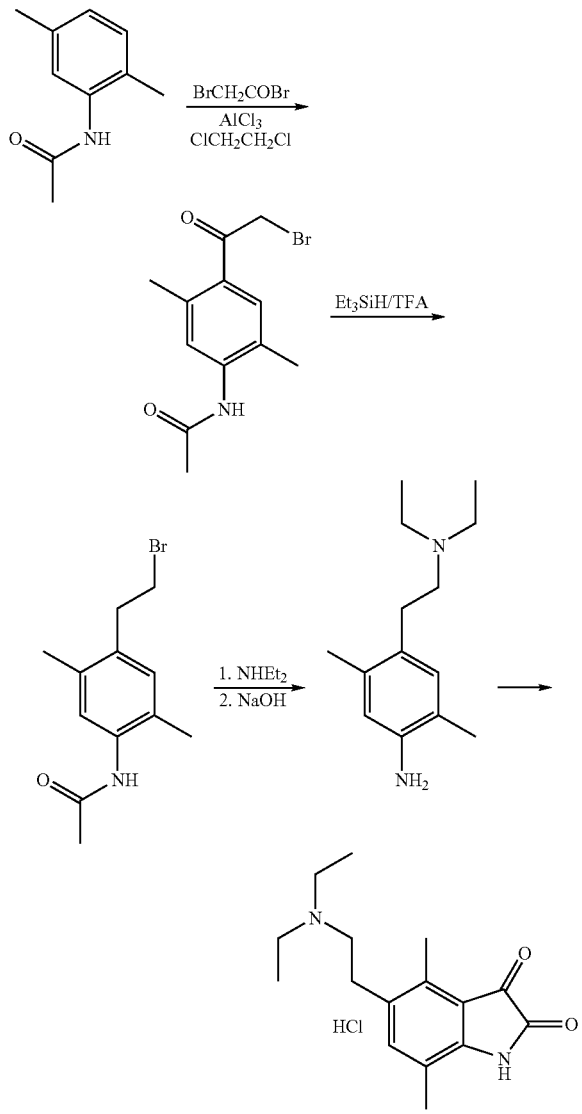

Step 1. N-[4-(2-Bromo-acetyl)-2,5-dimethyl-phenyl]-acetamide

Neat bromoacetyl bromide 40.11 g (198.7 mmol) was added into a stirred slurry of aluminum chloride 34.2 g (256.5 mmol) in anhydrous dichloroethane (40 mL) at 0° C. over 1 min period and the mixture was stirred on ice bath for 1 hour under dry nitrogen. A solution prepared by dissolving 2,5-dimethylacetanilide 16.624 g (101.85 mmol) in hot anhydrous dichloroethane (80 mL) was added while hot (quickly, in order to prevent the starting acetanilide solution from congealing) into the ice-cooled aluminum chloride mixture and the obtained homogenous mixture was stirred at 0–5° C. for 90 minutes (the ice bath was allowed to melt) and at 5–10° C. for 30 minutes and then at 10° C. to room temperature for additional 4½ hours under nitrogen. The reaction mixture was poured onto crushed ice in a large beaker, stirred for 10 minutes. The aqueous phase was poured off, the remaining white sticky semi-solid material was mixed with hexane (0.7 L) and the mixture was stirred for 15 minutes.

The precipitate was collected by filtration, washed with plenty of hexane and water (repeatedly), compressed on the frit, washed again with water, then dried by air suction, then on high vacuum (2 days).

Y=29.08 g (100%) of a white solid.

The material contained 3% of the analogous chloroacetyl product as an impurity.

$^1$H-NMR (DMSO-$d_6$, 400 MHz): δ 9.355 (br s, 1H), 7.771 (s, 1H), 7.542 (s, 1H), 4.823 (s, 2H), 2.363 (s, 3H), 2.234 (s, 3H), 2.096 (s, 3H).

Step 2: N-[4-(2-Bromo-ethyl)-2,5-dimethyl-phenyl]-acetamide

Triethylsilane 60 mL (375 mmol) was added to trifluoroacetic acid 360 mL and stirred until a homogenous mixture was obtained (15 minutes). This mixture was then added to solid N-[4-(2-bromo-acetyl)-2,5-dimethyl-phenyl]-acetamide 28.88 g (101.64 mmol) in an ice-cooled flask. The flask was capped with a Dryerite-filled tube (as a gas outlet) and the mixture was stirred on ice bath for 1 hour, then at room temperature for 1 day. The reaction mixture was evaporated and the obtained thick residue was suspended in hexane (0.3 L). Water (100 mL) was added and the mixture was stirred and occasionally shaken for about 1 hour. The formed precipitate was collected by filtration, washed repeatedly with plenty of hexane and water, compressed on the frit, dried by air suction, then on high vacuum.

Y=27.30 g of a white solid (99.5%).

The material contained 3% of the analogous chloroethyl product, which originated from impurity in the starting material.

$^1$H-NMR (DMSO-$d_6$, 400 MHz): δ 9.175 (br s, 1H), 7.163 (s, 1H), 7.025 (s, 1H), 3.641 (t, J=7.4 Hz, 2H), 3.051 (t, J=7.8 Hz, 2H), 2.212 (s, 3H), 2.121 (s, 3H), 2.023 (s, 3H).

Step 3: N-[4-(2-Diethylamino-ethyl)-2,5-dimethyl-phenyl]-acetamide

A mixture of N-[4-(2-bromo-ethyl)-2,5-dimethyl-phenyl]-acetamide 9.00 g (33.3 mmol), diethylamine 150 mL and acetonitrile (110 mL) was stirred at reflux (oil bath) for 14 hours. The mixture was evaporated, the obtained solid was suspended in water (200 mL), made strongly alkaline with 15% aq. NaOH (20 mL) and the mixture was stirred and occasionally shaken for 6 hours. The solids were collected by filtration, compressed on the frit, washed with water and dried on highvac. (This was the fraction 1).

The filtrates were diluted with saturated aqueous sodium bicarbonate 100 mL and extracted with ethyl acetate (2×250 mL). The combined org, extracts were dried (magnesium sulfate) and evaporated. The solid residue was dried on highvac. (Fraction 2). The combined fractions (1+2) were dissolved in hot benzene (100 mL), the obtained cloudy solution was diluted with ether (200 mL), filtered, diluted with additional ether (200 mL). With stirring, 4M HCl in dioxane (20 mL) was added dropwise and the obtained slurry was stirred for 2 hours. The precipitated solids were collected by quick filtration, rinsed with ether and dried on high vacuum.

This crude acetanilide intermediate HCl salt (9.55 g, 96% Y) was dissolved in water (100 mL, with sonication) and the cloudy solution was filtered from a small amount of insoluble impurities (washed with additional water, 3×10 mL). The filtrates were concentrated down to approximatel 100 mL overall volume, concentrated hydrochloric acid (100 mL) was added and the mixture was refluxed on an oil bath (170–180° C.) for 2 hours. The reaction mixture was evaporated to dry and the residue was dried on high vacuum.

Y=8.101 g of a light-tan very hygroscopic solid (83% overall).

$^1$H-NMR (DMSO-$d_6$, 400 MHz): δ 10.982 (br s, 1H), 10.327 (br s, 3H), 7.244 (s, 1H), 7.175 (s, 1H), 3.160 (m, 6H), 3.028 (m, 2H), 2.311 (s, 3H), 2.292 (s, 3H), 1.250 (t, J=7.4 Hz, 6H).

Step 4: 5-(2-Diethylamino-ethyl)-4,7-dimethyl-1H-indole-2,3-dione hydrochloride 8.100 g of N-[4-(2-diethylamino-ethyl)-2,5-dimethyl-phenyl]-acetamide.2HCl (27.62 mmol), chloral hydrate 5.000 g (30.2 mmol) and sodium sulfate (anhydrous) 36 g was stirred in water 100 mL for 20 minutes. Hydroxylamine hydrochloride 6.25 g (90 mmol) in water 30 mL was added, the mixture was stirred at room temperature for 10 min, then placed on oil bath and stirred at 80–85° C. for 90 minutes. The react mixture was diluted with saturated NaCl (250 mL) and stirred at room temperature overnight. The precipitate was collected by filtration, washed with saturated NaCl, dried by air suction, then on highvac overnight.

The obtained dry intermediate (containing some salt) was added in small portions into 50 mL of an ice-cooled 5:1 (v/v) mixture of concentrated sulfuric acid (96%) and water, in a 0.5 L wide-mouth flask, over 10 minute period. (There was effervescence due to the HCl gas evolution). The cooling bath was removed and the mixture was stirred at room temperature until all chunks of the intermediate dissolved (2 hours). The formed dark thick mixture was then stirred on oil bath at 75–80° C. for 1 hour. The reaction mixture was cooled on ice bath and ice (1 handful) was added, followed after 10 minutes with saturated NaCl (450 mL). The deep purple mixture was stirred on ice bath for 3 hours. The precipitated solids were collected by filtration, washed with ice-cold saturated NaCl and dried by air suction and on highvac. The salt-containing product was extracted in a Soxhlet apparatus with mixture chloroform-anhydrous ethanol 1:1 (v/v), 200 mL, until all colorful material was extracted (oil bath, ½ day reflux). The extract was allowed to crystallize at room temperature overnight, the precipitated product first fraction (4.412 g) was collected by filtration, washed with anhydrous ethanol and dried on highvac. A second fraction (1.262 g) was collected by concentrating the supernatants to a small volume (approximatel 40 mL), re-heating to reflux, followed by crystallization overnight.

Combined yield: 5.674 g of an orange cryst. solid (66% overall).

$^1$H-NMR (DMSO-$d_6$, 400 MHz): δ 11.033 (s, 1H), 10.760 (br s, 1H), 7.289 (s, 1H), 3.162 (m, 4H), 3.050 (m, 2H), 2.983 (m, 2H), 2.461 (s, 3H), 2.136 (s, 3H), 1.248 (t, J=7.4 Hz, 6H).

Example 15

4,7-Dimethyl-5-(2-pyrrolidin-1-yl-ethyl)-1H-indole-2,3-dione hydrochloride

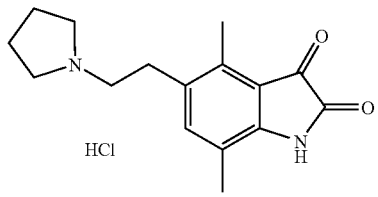

Step 1: 2,5-Dimethyl-4-(2-pyrrolidin-1-yl-ethyl)-phenylamine

A mixture of N-[4-(2-bromo-ethyl)-2,5-dimethyl-phenyl]-acetamide 9.00 g (33.3 mmol) and neat pyrrolidine 150 mL was stirred at 70° C. for 4½ hours. Evaporating the react mixture and drying the residue on highvac a solid was obtained. This material was dissolved in water (100 mL), treated with 15% aq. NaOH (20 mL) and cooled on ice bath for 1 hour. The precipitate was collected by filtration, washed with water and dried on highvac. (Fraction 1) The filtrates were diluted with saturated aqueous sodium bicarbonate 100 mL and extracted with ethyl acetate (2×250 mL). The combined org. extracts were dried (magnesium sulfate) and evaporated. The solid residue was dried on highvac. (Fraction 2).

The combined fractions were dissolved in hot benzene (100 mL), THF (100 mL) was added, diluted with ether (0.5 L). With stirring, 4M HCl in dioxane (20 mL) was added dropwise and the obtained slurry was stirred for 2 hours. The precipitated solids were collected by quick filtration, rinsed with ether and dried on highvac.

This crude acetanilide intermediate-HCl salt (9.85 g, 99.5% Y) was dissolved in water (70 mL, with 30 min stirring) and the obtained cloudy solution was filtered from a small amount of insoluble impurities (washed with additional water, 3×10 mL). The filtrates were combined with concentrated hydrochloric acid (100 mL) and the mixture was refluxed on oil bath (170–180° C.) for 2 hours. The reaction mixture was evaporated to driynes and the residue was dried on high vacuum.

Y=8.53 g of a light-tan hygroscopic solid (88% overall).

$^1$H-NMR (DMSO-$d_6$, 400 MHz): 11.315 (br s, 1H), 10.281 (br s, 3H), 7.233 (s, 1H), 7.150 (s, 1H), 3.529 (m, 2H), 3.204 (m, 2H), 3.014 (m, 4H), 2.301 (s, 3H), 2.287 (s, 3H), 1.999 (m, 2H), 1.883 (m, 2H).

Step 2: 4,7-Dimethyl-5-(2-pyrrolidin-1-yl-ethyl)-1H-indole-2,3-dione hydrochloride 8.35 g of 2,5-dimethyl-4-(2-pyrrolidin-1-yl-ethyl)-phenylamine. 2HCl (29.29 mmol) 5.293 g of chloral hydrate (32 mmol) and 38 g of sodium sulfate (anhydrous) was suspended in water 100 mL, hydroxylamine hydrochloride 6.60 g (95 mmol) and water 40 mL was added and the mixture was refluxed under nitrogen on oil bath (140–150° C.) for 1 hour. The reaction mixture was stirred at room temperature overnight, the-precipitated solids were collected by filtration (without washing) and dried by air suction, then on highvac. The obtained intermediate was added in small portions into 50 mL of an ice-cooled 5:1 (v/v) mixture of concentrated sulfuric acid (96%) and water, in a 0.5L wide-mouth flask, over 10 minute period. The cooling bath was removed and the mixture was stirred at room temperature until all chunks of the intermediate dissolved (1 hour). The formed dark thick mixture was then stirred on an oil bath at 75–80° C. for 1 hour. The reaction mixture was cooled on ice bath and ice (1 handful) was added, followed after 10 minutes with saturated NaCl (250 mL).

The rest of the procedure was practically identical to the above preparation of 5-(2-Diethylamino-ethyl)-4,7-dimethyl-1H-indole-2,3-dione hydrochloride.

Combined product yield was 4.536 g (50% overall) of a brick-red crystalline solid.

$^1$H-NMR (DMSO-$d_6$, 400 MHz): δ 11.100 (br s, 1H), 11.028 (s, 1H), 7.266 (s, 1H), 3.530 (m, 2H), 3.181 (m, 2H), 3.014 (m, 2H), 2.975 (m, 2H), 2.455 (s, 3H), 2.132 (s, 3H), 2.000 (br m, 2H), 1.882 (m, 2H).

Example 16

4,7-Dimethyl-5-(2-morpholin-4-yl-ethyl)-1H-indole-2,3-dione hydrochloride

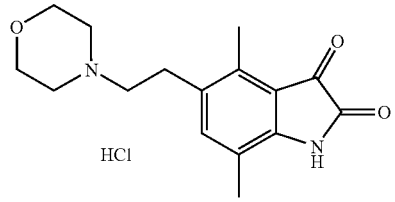

Step 1: 2,5-Dimethyl-4-(2-morpholin-4-yl-ethyl)-phenylamine hydrochloride

A mixture of N-[4-(2-bromo-ethyl)-2,5-dimethyl-phenyl]-acetamide 9.00 g (33.3 mmol) and neat morpholine 150 mL was stirred at 70° C. for 6 hours. Evaporating the reaction mixture and drying the residue on highvac, a solid was obtained. The material was dissolved in boiling water (50 mL), treated with 15% aq. NaOH (20 mL) and cooled on ice bath for 3 hours. The precipitate (a small amount of material, mostly the impurities) was collected by filtration, washed with water and discarded. The filtrates were diluted with saturated aqueous sodium bicarbonate 100 mL and extracted repeatedly with large volume of ethyl acetate (8×250 mL). The combined org. extracts were dried (magnesium sulfate) and evaporated. The solid residue was dried on highvac. The material was dissolved in refluxing benzene (100 mL), diluted with hot hexane (200 mL) and stirred at room temperature overnight. The formed precipitate was collected by filtration, washed with hexane and dried on high vacuum. (Fraction 1, 7.888 g). The benzene/hexane supernatants were evaporated to driynes, the residue dissolved in hot benzene (50 mL), the solution diluted with hot hexane (150 mL) and allowed to crystallize overnight. The precipitated material was collected by filtration, washed with hexane and dried on high vacuum. (Fraction 2, 0.570 g)

The combined fractions (1+2) of this acetanilide intermediate (8.458 g, 92%) were dissolved in water 80 mL, concentrated hydrochloric acid 80 mL was added. The mixture was refluxed on oil bath (170–180° C.) for 3 hours. The reaction mixture was evaporated to driynes and the residue was dried on high vacuum.

Y=9.343 g of a pale yellow hygroscopic solid (92% overall.

$^1$H-NMR (DMSO-$d_6$, 400 MHz): δ 11.593 (br s, 1H), 10.072 (br s, 3H), 7.194 (s, 1H), 7.115 (s, 1H), 3.964 (br m, 2H), 3.840 (br m, 2H), 3.490 (br d, 2H), 3.162 (br m, 2H), 3.063 (m, 4H), 2.290 (s, 6H).

Step 2: 4,7-Dimethyl-5-(2-morpholin-4-yl-ethyl)-1H-indole-2,3-dione hydrochloride 8.100 g of 2,5-dimethyl-4-(2-morpholin-4-yl-ethyl)-phenylamine.2HCl (27.62 mmol), chloral hydrate 5.000 g (30.2 mmol) and sodium sulfate (anhydrous) 36 g was stirred in water 100 mL for 20 minutes. Hydroxylamine hydrochloride 6.25 g (90 mmol) in water 30 mL was added, the mixture was stirred at room temperature for 10 min, then placed on oil bath and stirred at 80–85° C. for 90 minutes. The react. mixture was diluted with saturated NaCl (250 mL) and stirred at room temperature overnight. The precipitate was collected by filtration, washed with saturated NaCl, dried by air suction, then on high vacuum overnight.

The obtained dry intermediate (containing some salt) was added in small portions into 50 mL of an ice-cooled 5:1 (v/v) mixture of concentrated sulfuric acid (96%) and water, in a 0.5 L wide-mouth flask, over 10 minute period. (There was effervescence due to the HCl gas evolution). The cooling bath was removed and the mixture was stirred at room temperature until all chunks of the intermediate dissolved (2 hours). The formed dark thick mixture was then stirred on oil bath at 75–80° C. for 1 hour. The reaction mixture was cooled on ice bath and ice (1 handful) was added, followed after 10 minutes with saturated NaCl (450 mL). The deep purple mixture was stirred on ice bath for 3 hours. The precipitated solids were collected by filtration, washed with ice-cold saturated NaCl and dried by air suction and on highvac. The salt-containing product was extracted in a Soxhlet apparatus with mixture chloroform-anhydrous ethanol 1:1 (v/v), 200 mL, until all colorful material was extracted (oil bath, ½ day reflux). The extract was allowed to crystallize at room temperature overnight, the precipitated product first fraction (4.412 g) was collected by filtration, washed with anhydrous ethanol and dried on highvac. A second fraction (1.262 g) was collected by concentrating the supernatants to a small volume (approximatel 40 mL), re-heating to reflux, followed by crystallization overnight.

Combined yield: 5.674 g of an orange cryst. solid (66% overall). $^1$H-NMR (DMSO-d$_6$, 400 MHz): δ 11.033 (s, 1H), 10.760 (br s, 1H), 7.289 (s, 1H), 3.162 (m, 4H), 3.050 (m, 2H), 2.983 (m, 2H), 2.461 (s, 3H), 2.136 (s, 3H), 1.248 (t, J=7.4 Hz, 6H).

Example 17

4-(9H-1,2,3a,4,9,10-Hexaaza-cyclopenta[b]fluoren-3-ylmethyl)-phenol

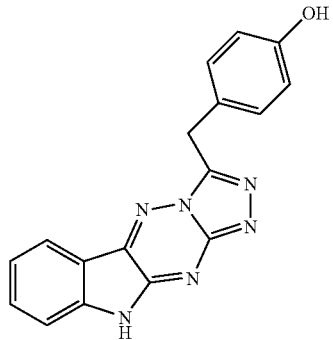

In a pressure tube, 74 mg of 1H-indole-2,3-dione (0.500 mmol) and 103 mg of 4-(4,5-diamino-4H-[1,2,4]triazol-3-ylmethyl)-phenol (0.500 mmol) in a mixture of trifluoroethanol (8 mL) and water (4 mL) was stirred at 125° C. overnight (19 hr). The mixture was cooled to room temperature, allowed to crystallize for 3 hours. The precipitated product was collected by filtration, washed with MeOH+water 1:1, then with MeOH and dried on high vacuum.

Y=126 mg of a yellow solid (79.5%).

[An analogous parallel experiment performed in a mixture EtOH (4 mL) plus water (4 mL) plus AcOH (0.10 mL) yielded 126 mg (79.5%) of the identical product].

MS+cAPCI: 317(M+1).

MS−cAPCI: 315(M−1).

$^1$H-NMR(DMSO-d$_6$, 400 MHz): δ 12.187 (br s, 1H), 9.261 (s, 1H), 8.151 (app d, J=7.4 Hz, 1H), 7.701 (app t, J=7.2 Hz, 1H), 7.417 (app d, J=8.2 HZ, 1H), 7.324 (app t, J=7.8 Hz, 1H), 7.180 (app d, J=8.6 Hz, 2H), 6.685 (app d, J=8.6 Hz, 2H), 4.413 (s, 2H).

Example 18

4-(5,8-Dichloro-9H-1,2,3a,4,9,10-hexaaza-cyclopenta[b]fluoren-3-ylmethyl)-phenol (General Cyclization Procedure)

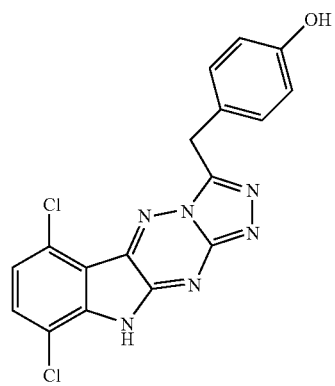

In a pressure tube, 0.60 mmol of 4,7-dichloro-1H-indole-2,3-dione (130 mg) and 0.65 mmol of 4-(4,5-diamino-4H-[1,2,4]triazol-3-ylmethyl)-phenol (133.5 mg) in a mixture of trifluoroethanol (8 mL) and water (4 mL) was stirred at 125° C. overnight (16 hr). The mixture was cooled to room temperature, allowed to crystallize for 2 hours. The precipitated product was collected by filtration, washed with MeOH+water 1:1, then with chilled MeOH. Dried on high vacuum.

Y=209 mg of a deep yellow solid (90.5%).

MS+cAPCI: 387, 385 (M+1).

MS−cAPCI: 385, 383 (M−1).

$^1$H-NMR(DMSO-d$_6$, 400 MHz): δ 12.864 (br s, 1H), 9.259 (s, 1H), 7.797 (d, J=8.6 Hz, 1H), 7.406 (d, J=8.6 Hz, 1H), 7.250 (app d, J=8.6 Hz, 2H), 6.674 (app d, J=8.6 Hz, 2H), 4.408 (s, 2H).

Example 19

4-(5-Chloro-6-methoxy-9H-1,2,3a,4,9,10-hexaaza-cyclopenta[b]fluoren-3-ylmethyl)-phenol

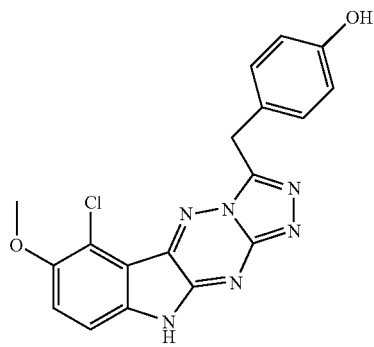

According to the general cyclization procedure (for Example 18), 127 mg of 4-chloro-5-methoxy-1H-indole-2,3-dione (0.6 mmol) was used for the preparation.

Y=190 mg of a light-red solid (83%).

MS+cAPCI: 383, 381 (M+1).

MS−cAPCI: 381, 379 (M−1).

$^1$H-NMR(DMSO-d$_6$, 400 MHz): δ 12.178 (br s, 1H), 9.251 (s, 1H), 7.528 (d, J=9.0 Hz, 1H), 7.331 (d, J=8.6 Hz, 1H), 7.248 (app d, J=8.6 Hz, 2H), 6.668 (app d, J=8.6 Hz, 2H), 4.387 (s, 2H), 3.932 (s, 3H).

Example 20

4-(5,8-Dichloro-6-methoxy-9H-1,2,3a,4,9,10-hexaaza-cyclopenta[b]fluoren-3-ylmethyl)-phenol

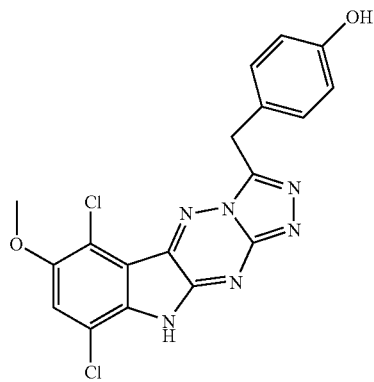

According to the general cyclization procedure (for Example 18), 148 mg of 4,7-dichloro-5-methoxy-1H-indole-2,3-dione (0.6 mmol) was used for the preparation.

Y=239 mg of a light-red solid (96%).

MS+cAPCI: 417, 415 (M+1).

MS−cAPCI: 415, 413 (M−1).

$^1$H-NMR(DMSO-d$_6$, 400 MHz): δ 12.588 (br s, 1H), 9.253 (s, 1H), 7.659 (s, 1H), 7.245 (app d, J=8.6 Hz, 2H), 4.393 (s, 3H), 3.953 (s, 3H)

Example 21

4-(5-Chloro-9H-1,2,3a,4,9,10-hexaaza-cyclopenta[b]fluoren-3-ylmethyl)-phenol

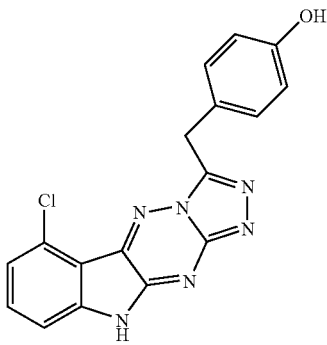

According to the general cyclization procedure (for Example 18), 109 mg of 4-chloro-1H-indole-2,3-dione (0.6 mmol) was used for the preparation.

Y=175 mg of a yellow solid (83%).

MS+cAPCI: 353, 351 (M+1).

MS−cAPCI: 353, 349 (M−1).

$^1$H-NMR(DMSO-d$_6$, 400 MHz): δ 12.426 (br s, 1H), 9.252 (s, 1H), 7.682 (app t, J=8.2 Hz, 1H), 7.390 (app d, J=3.1 Hz, 1H), 7.370 (app d, J=2.8 Hz, 1H), 7.250 (app d, J=8.6 Hz, 2H), 6.672 (app d, J=8.6 Hz, 2H), 4.396 (s, 2H).

Example 22

4-(8-Chloro-9H-1,2,3a,4,9,10-hexaaza-cyclopenta[b]fluoren-3-ylmethyl)-phenol

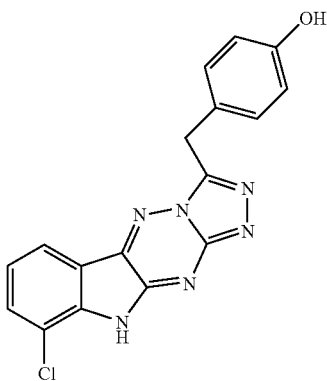

According to the general cyclization procedure (for Example 18), 109 mg of 7-chloro-1H-indole-2,3-dione (0.6 mmol) was used for the preparation.

Y=195 mg of a yellow solid (92.5%).

MS+cAPCI: 353, 351 (M+1).

MS−cAPCI: 353, 349, 348 (M−1).

$^1$H-NMR(DMSO-d$_6$, 400 MHz): δ 12.628 (br s, 1H), 9.265 (s, 1H), 8.140 (dd, J=7.8 Hz, J=1.2 Hz, 1H), 7.799 (dd, J=7.8 Hz, J=1.2 Hz, 1H), 7.335 (app t, J=7.8 Hz, 1H), 7.184 (app d, J=8.6 Hz, 2H), 6.686 (app d, J=8.6 Hz, 2H), 4.424 (s, 2H).

Example 23

4-(5,6,8-Trichloro-9H-1,2,3a,4,9,10-hexaaza-cyclopenta[b]fluoren-3-ylmethyl)-phenol

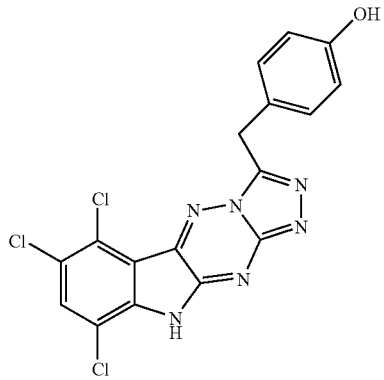

According to the general cyclization procedure (for Example 18), 150.5 mg of 4,5,7-trichloro-1H-indole-2,3-dione (0.6 mmol) was used for the preparation.

Y=237 mg of a yellow solid (94%).

MS+cAPCI: 353, 351 (M+1).

MS−cAPCI: 353, 349, 348 (M−1).

$^1$H-NMR(DMSO-$d_6$, 400 MHz): 13.016 (br s, 1H), 9.259 (s, 1H), 8.194 (s, 1H), 7.252 (app d, J=8.6 Hz, 2H), 6.677 (app d, J=8.6 Hz, 2H), 4.419 (s, 2H).

Example 24

4-(5,8-Dimethyl-9H-1,2,3a,4,9,10-hexaaza-cyclopenta[b]fluoren-3-ylmethyl)-phenol, dihydrate

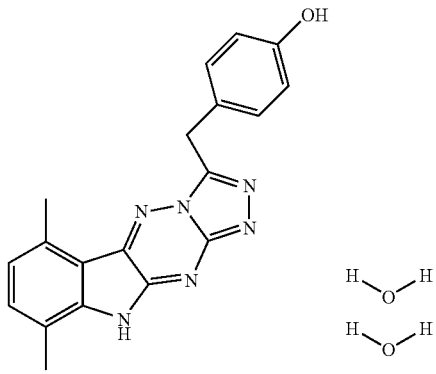

According to the general cyclization procedure (for Example 18), 105.5 mg of 4,7-dimethyl-1H-indole-2,3-dione (0.6 mmol) was used for the preparation.

Y=67.5 mg of a light brown solid (29.5%).

MS+cAPCI: 345 (M+1).

MS−cAPCI: 343 (M−1).

$^1$H-NMR(DMSO-$d_6$, 400 MHz): δ 12.107 (br s, 1H), 9.257 (s, 1H), 7.367 (br d, J=7.8 Hz, 1H), 7.215 (app d, J=8.6 Hz, 2H), 7.024 (br d, J=7.4 Hz, 1H), 6.678 (app d, J=8.6 Hz, 2H), 4.393 (s, 2H), 3.318 (s, 4H), 2.738 (s, 3H), 2.408 (s, 3H).

Example 25

4-(6,8-Dimethyl-9H-1,2,3a,4,9,10-hexaaza-cyclopenta[b]fluoren-3-ylmethyl)-phenol

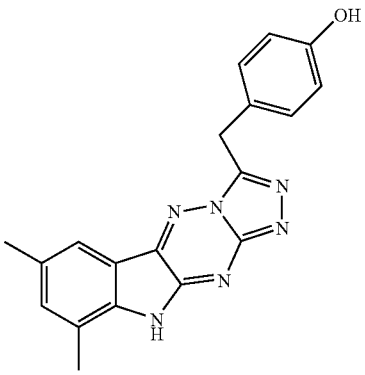

According to the general cyclization procedure (for Example 18), 105.5 mg of 5,7-dimethyl-1H-indole-2,3-dione (0.6 mmol) was used for the preparation.

Y=159 mg of a yellow solid (77%).

MS+cAPCI: 345 (M+1).

MS−cAPCI: 343, 342 (M−1).

$^1$H-NMR(DMSO-$d_6$, 400 MHz): δ 12.049 (br s, 1H), 9.264 (s, 1H), 7.742 (br s, 1H), 7.315 (br s, 1H), 7.179 (app d, J=8.6 Hz, 2H), 6.690 (app d, J=8.6 Hz, 2H), 4.396 (s, 2H), 2.416 (s, 3H), 2.385 (s, 3H).

Example 26

4-(6-Chloro-8-methyl-9H-1,2,3a,4,9,10-hexaaza-cyclopenta[b]fluoren-3-ylmethyl)-phenol

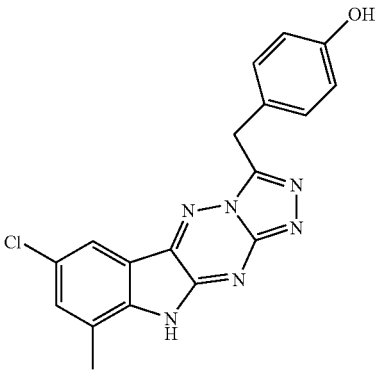

According to the general cyclization procedure (for Example 18), 117.5 mg of 5-chloro-7-methyl-1H-indole-2,3-dione (0.6 mmol) was used for the preparation.

Y=201 mg of a yellow solid (92%).

MS+cAPCI: 367, 365 (M+1).

MS−cAPCI: 365, 363 (M−1).

$^1$H-NMR(dDMSO, 400 MHz): δ 12.332 (br s, 1H), 9.263 (s, 1H), 8.025 (br d, J=2.0 Hz, 1H), 7.598 (br m, 1H), 7.202 (app d, J=8.6 Hz, 2H), 6.690 (app d, J=8.6 Hz, 2H), 4.404 (s, 2H), 2.466 (s, 3H).

Example 27

5,8-Dichloro-3-(4-fluoro-benzyl)-9H-1,2,3a,4,9,10-hexaaza-cyclopenta[b]fluorine (General Cyclization Procedure)

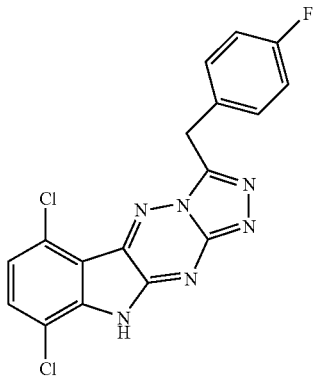

In a pressure tube, 0.60 mmol of 4,7-dichloro-1H-indole-2,3-dione (130 mg) and 0.70 mmol of 5-(4-fluoro-benzyl)-[1,2,4]triazole-3,4-diamine (145 mg) in a mixture of trifluoroethanol (8 mL) and water (4 mL) was stirred at 125° C. overnight (14 hr). The mixture was cooled to room temperature, allowed to crystallize for 2 hours. The precipitated product was collected by filtration, washed with MeOH+water 1:1, then with chilled MeOH. Dried on high vacuum.

Y=209 mg of a deep yellow solid (90%).

$^1$H-NMR(DMSO-$d_6$, 400 MHz): δ 12.858 (s, 1H), 7.780 (d, J=8.6 Hz, 1H), 7.476 (app dd, J=8.7 Hz, J=5.5 Hz, 2H), 7.386 (d, J=8.6 Hz, 1H), 7.126 (app t, J=8.6 Hz, 2H), 4.536 (s, 2H); $^{19}$F-NMR(DMSO-$d_6$, 376.5 MHz): δ-116.30 (m, 1F).

Example 28

5-Chloro-3-(4-fluoro-benzyl)-8-methyl-9H-1,2,3a,4,9,10-hexaazacyclopenta[b]fluorene

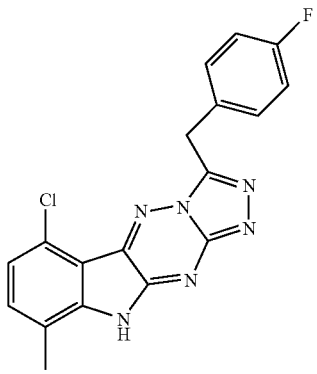

According to the general cyclization procedure (for Example 27), 0.60 mmol of 4-chloro-7-methyl-1H-indole-2,3-dione (117.5 mg) and 0.70 mmol of 5-(4-fluoro-benzyl)-[1,2,4]triazole-3,4-diamine (145 mg) was used for the preparation.

Y=188 mg of a yellow solid (85.5%).

$^1$H-NMR(DMSO-$d_6$, 400 MHz): δ 12.388 (s, 1H), 7.494 (m, 1H), 7.474 (m, 2H), 7.263 (d, J=7.8 Hz, 1H), 7.123 (app t, J=9.0 Hz, 2H), 4.520 (s, 2H), 2.443 (s, 3H); $^{19}$F-NMR (DMSO-$d_6$, 376.5 MHz): δ-116.36 (m, 1F).

Example 29

5,8-Dichloro-3-(4-fluoro-benzyl)-6-methoxy-9H-1,2,3a,4,9,10-hexaaza-cyclopenta[b]fluorene

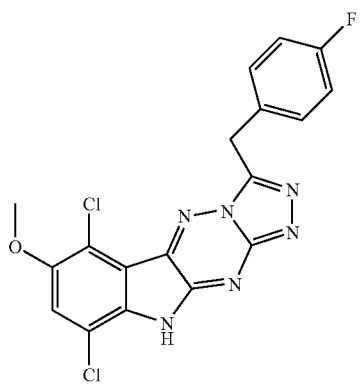

According to the general cyclization procedure (for Example 27), 0.60 mmol of 4,7-dichloro-1H-indole-2,3-dione (148 mg) and 0.70 mmol of 5-(4-fluoro-benzyl)-[1,2,4]triazole-3,4-diamine (145 mg) was used for the preparation.

Y=240 mg of a bright-red solid (96%).

$^1$H-NMR(DMSO-$d_6$, 400 MHz): 6 12.576 (s, 1H), 7.634 (s, 1H), 7.473 (app dd, J=8.6 Hz, J=5.5 Hz, 2H), 7.119 (app t, J=8.6 Hz, 2H), 4.520 (s, 2H), 3.941 (s, 3H); $^{19}$F-NMR (DMSO-$d_6$, 376.5 MHz): δ-116.32 (m, 1F).

Example 30

3-(4-Fluoro-benzyl)-5,8-dimethyl-9H-1,2,3a,4,9,10-hexaaza-cyclopenta[b]fluorene

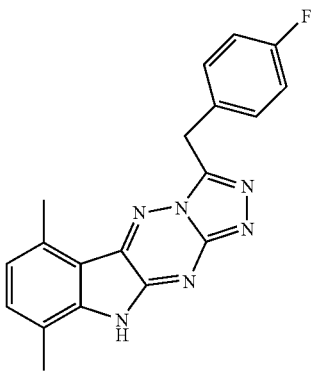

According to the general cyclization procedure (for Example 27), 0.60 mmol of 4,7-dimethyl-1H-indole-2,3-dione (105 mg) and 0.70 mmol of (4-fluoro-benzyl)-[1,2,4]triazole-3,4-diamine (145 mg) in 2 mL of ethylene glycol was stirred at 125° C. overnight (18 hr). The mixture was cooled to room temperature, diluted with water (10 mL), stirred for 15 min. The precipitated product was collected by filtration, washed with MeOH+water 1:1. Dried on high vacuum. The crude product (187 mg) was suspended in anhydrous ethanol (6 mL), heated to reflux, sonicated while hot, allowed to cool overnight, filtered, washed with ice-cold methanol, filtered and dried on high vacuum.

Y=165 mg of a orange-brown solid (79.5%).

MS+cESI: 347 (M+1).

MS+cESI: 345 (M−1).

$^1$H-NMR(DMSO-d$_6$, 400 MHz): δ 12.094 (s, 1H), 7.444 (dd, J=8.6 Hz, J=5.5 Hz, 2H), 7.344 (d, J=7.8 Hz, 1H), 7.127 (app t, J=9.0 Hz, 2H), 6.999 (d, J=7.8 Hz, 1H), 4.520 (m, 2H). 2.710 (s, 3H), 2.401 (s, 3H); $^{19}$F-NMR(DMSO-d$_6$) 376.5 MHz): δ-116.41 (m, 1F).

Example 31

4-(5-Chloro-8-methyl-9H-1,2,3a,4,9,10-hexaaza-cyclopenta[b]fluoren-3-ylmethyl)-phenol

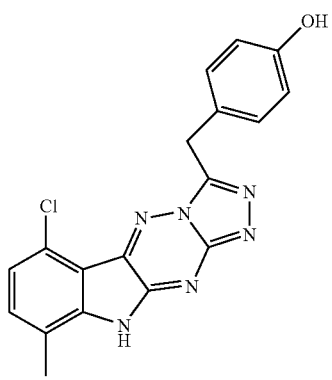

According to the general cyclization procedure (for Example 27), 0.60 mmol of 4-chloro-7-methyl-1H-indole-2,3-dione (117.5 mg) and 0.70 mmol of 4-(4,5-diamino-4H-[1,2,4]triazol-3-ylmethyl)-phenol (144 mg) was used for the preparation.

Y=157 mg of a bright-yellow solid (71.5%).

MS+APCI: 365 (M+1), 729 (2M+1).

MS−APCI: 363 (M−1), 727 (2M−1).

$^1$H-NMR(DMSO-d$_6$, 400 MHz): δ 12.368 (s, 1H), 9.236 (s, 1H), 7.476 (app d, J=8.6 Hz, 1H), 7.252 (app t, J=7.8 Hz, 3H), 6.662 (app d, J=8.6 Hz, 2H), 4.387 (s, 2H), 2.440 (s, 3H).

Example 32

5-Chloro-3-(4-fluoro-benzyl)-9H-1,2,3a,4,9,10-hexaaza-cyclopenta[b]fluoren-6-ol

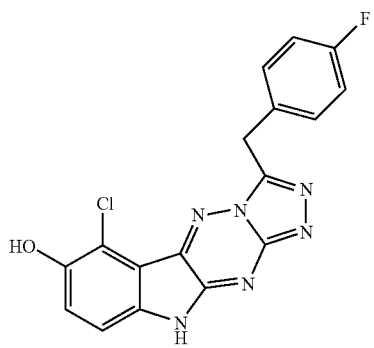

According to a cyclization procedure for Example 30, 0.60 mmol of 4-chloro-5-hydroxy-1H-indole-2,3-dione (118.5 mg) and 0.70 mmol of (4-fluoro-benzyl)-[1,2,4]triazole-3,4-diamine (145 mg) in 2 mL of ethylene glycol was stirred at 125° C. overnight (16 hr).

Y=170 mg of a brown solid (77%).

MS+cAPCI: 369 (M+1), 737 (2M+1).

MS−cAPCI: 367 (M−1), 735 (2M−1).

$^1$H-NMR(DMSO-d$_6$, 400 MHz): δ 12.078 (br s, 1H), 10.229 (s, 1H), 7.477 (app dd, J=8.6 Hz, J=5.4 Hz, 2H), 7.319 (d$_{AB}$, J=8.6 Hz, 1H), 7.210 (d$_{AB}$, J=8.6 Hz, 1H), 7.477 (app dd, J=8.6 Hz, 2H), 4.512 (s, 2H); $^{19}$F-NMR(DMSO-d$_6$, 376.5 MHz): δ-116.40 (m, 1F).

Example 33

5-Chloro-3-(4-hydroxy-benzyl)-9H-1,2,3a,4,9,10-hexaaza-cyclopenta[b]fluoren-6-ol

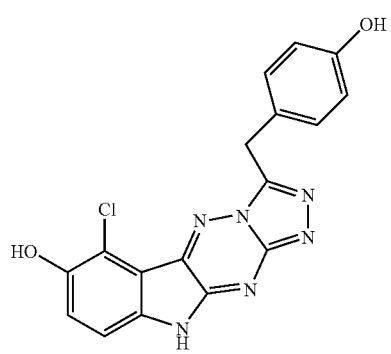

According to a cyclization procedure for Example 30, 0.60 mmol of 4-chloro-5-hydroxy-1H-indole-2,3-dione (118.5 mg) and 0.70 mmol of 4-(4,5-diamino-4H-[1,2,4]triazol-3-ylmethyl)-phenol (144 mg) in 2 mL of ethylene glycol was stirred at 125° C. overnight (16 hr).

Y=178 mg of a light-brown solid (81%).

MS+cAPCI: 367 (M+1), 733 (2M+1).

MS−cAPCI: 365 (M−1), 731 (2M−1).

$^1$H-NMR(DMSO-d$_6$, 400 MHz): δ 12.054 (br s, 1H), 10.226 (br s, 1H), 9.232 (s, 1H) 7.317 (d$_{AB}$, J=8.6 Hz, 1H), 7.239 (app d, J=8.2 Hz, 2H), 7.206 (d$_{AB}$, J=8.6 Hz, 1H), 6.658 (app d, J=8.7 Hz, 2H), 4.377 (s, 2H).

Example 34

[(3S)-3-Amino-pyrrolidin-1-yl]-[5-chloro-3-(4-fluoro-benzyl)-9H-1,2,3a,4,9,10-hexaaza-cyclopenta[b]fluoren-6-yl]-methanone

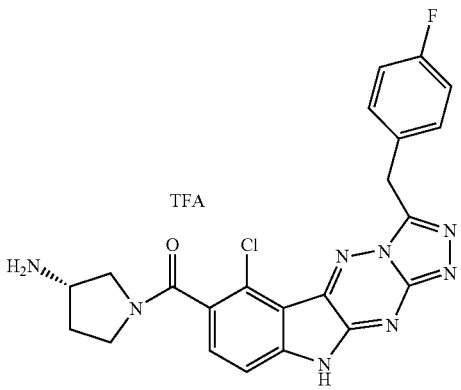

Step 1.

-continued

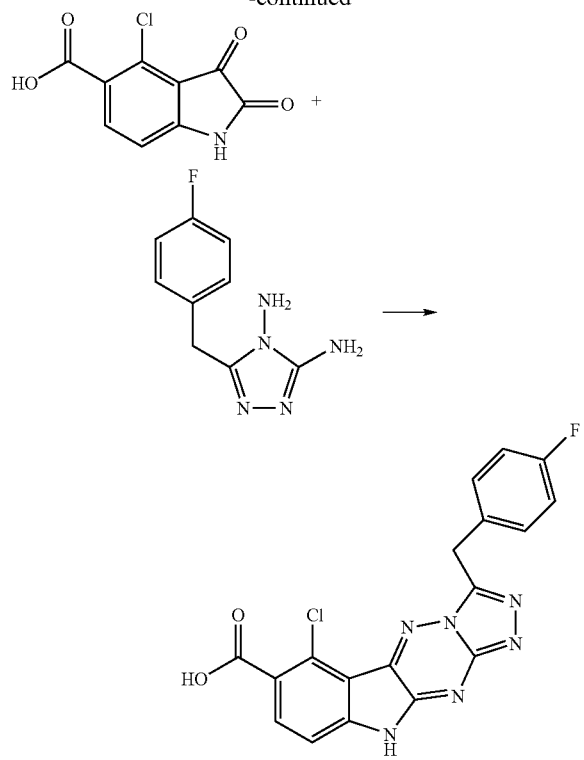

4-Chloro-2,3-dioxo-2,3-dihydro-1H-indole-5-carboxylic acid (114 mg, 0.51 mmol) and 5-(4-fluoro-benzyl)-[1,2,4]triazole-3,4-diamine (105 mg, 0.51 mmol) were dissolved in Ethanol. It was refluxed for 24 h. The reaction mixture was cooled to rt. The precipitate was filtered and washed with ethanol. The title compound was obtained in good purity.

$^1$H NMR (400 MHz, d$_6$-DMSO) δ 4.54 (s, 2H), 7.11–7.15 (m, 2H), 7.41 (d, J=8.6 Hz, 1H), 7.47–7.51 (m, 2H), 8.15 (d, J=8.6 Hz, 1H), 13.04 (vbr s, 1H); $^{19}$F NMR (377 MHz, d$_6$-DMSO) δ-116.3 (m, 1F).

Step 2.

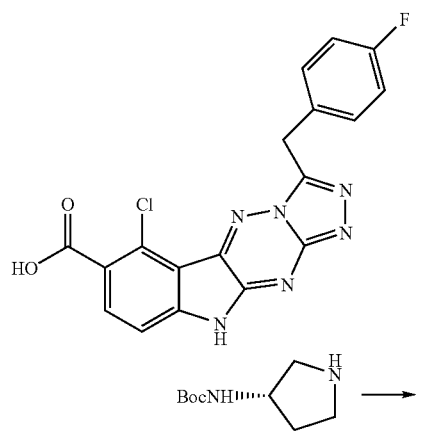

-continued

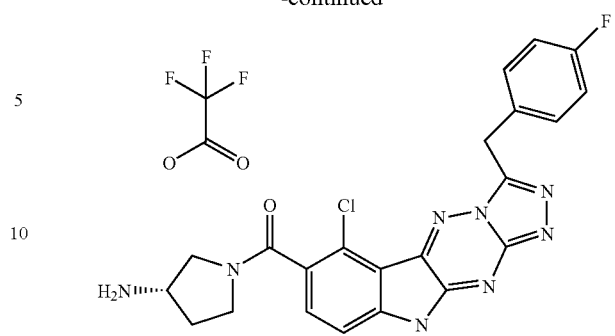

5-Chloro-3-(4-fluoro-benzyl)-9H-1,2,3a,4,9,10-hexaaza-cyclopenta[b]fluorene-6-carboxylic acid (68.5 mg, 0.17 mmol), Pyrrolidin-3-yl-carbamic acid tert-butyl ester (49 mg, 0.26 mmol), HOBt (38.5 mg, 0.29 mmol), EDC (46 mg, 0.24 mmol), and TEA (57 µl, 0.41 mmol) were dissolved in DMF (3 mL). It was stirred for 24 h at rt. DMF was removed and dichloromethane was added. It was washed with saturated sodiumbicarbonate and dried over sodiumsulfate. The solvent was removed and the residue was purified by chromatotron (15% methanol in dichloromethane).

The BOC group was cleaved with 10% TFA in Dichloromethane. The solvent was removed and the residue was lyophilized. The title compound was obtained as a fluffy yellow solid (59%).

$^1$H NMR (400 MHz, d$_6$-DMSO, mixture of two rotamers) δ 1.88–1.98 (m, 1H), 2.14–2.26 (m, 1H), 3.12–3.24 (m, 1H), 3.29–3.33 (m, 0.5H), 3.45 (dd, J=6.1, 11.2 Hz, 0.5H), 3.52–3.59 (m, 1H), 3.64–3.69 (m, 0.5H), 3.73–3.78 (m, 1H), 3.85 (br s, 0.5H), 4.46 (s, 2H), 7.05 (t, J=8.8 Hz, 2H), 7.38–7.42 (m, 3H), 7.63 (dt, J=1.6, 7.1 Hz, 1H), 7.94 (br s, 1.5H), 8.03 (br s, 1.5H), 12.56 (br s, 1H); $^{19}$F NMR (377 MHz, d$_6$-DMSO) δ-74.4 (s, 3F), −116.3 (m, 1F); MS m/z (relative intensity, %) 465.3 ([M+1]$^+$, 100).

Example 35

4-[5,8-Dimethyl-6-(2-morpholin-4-yl-ethoxy)-9H-1,2,3a,4,9,10-hexaaza-cyclopenta[b]fluoren-3-ylmethyl]-phenol

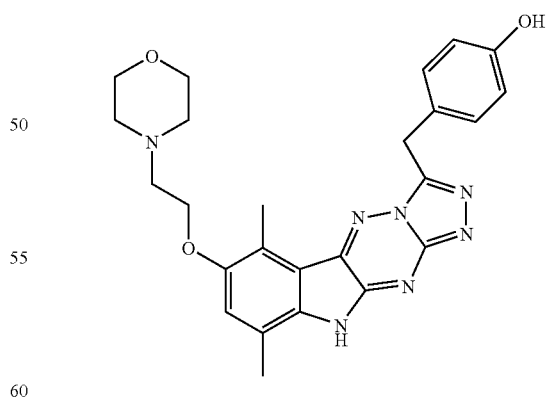

A mixture of 4,7-dimethyl-5-(2-morpholin-4-yl-ethoxy)-1H-indole-2,3-dione (121.6 mg, 0.4 mmol) and 4-(4,5-diamino-4H-[1,2,4]triazol-3-ylmethyl)-phenol (82 mg, 0.4 mmol) in EtOH (15 mL) was heated with stirring in a pressure tube at 120° C. for 72 h. The solvent was removed and the residue was purified with a flash silica gel chromatography (CH$_2$Cl$_2$:MeOH:NH$_4$OH=100:7:0.7) to give the title compound as a pink solid (50 mg, 27%).

$^1$H-NMR (400 MHz, DMSO-d$_6$) δ 11.87 (s, 1H), 9.23 (s, 1H), 7.18 (d, 2H), 7.17 (s, 1H), 6.65 (d, 2H), 4.36 (s, 2H), 4.10 (t, 2H), 3.58 (t, 4H), 2.72 (t, 2H), 2.61 (s, 3H), 2.49 (m, 4H), 2.40 (s, 3H). MS (m/z) 474 [M+1].

Example 36

3-(4-Fluoro-benzyl)-5,8-dimethyl-6-(2-morpholin-4-yl-ethoxy)-9H-1,2,3a,4,9,10-hexaaza-cyclopenta[b]fluorine

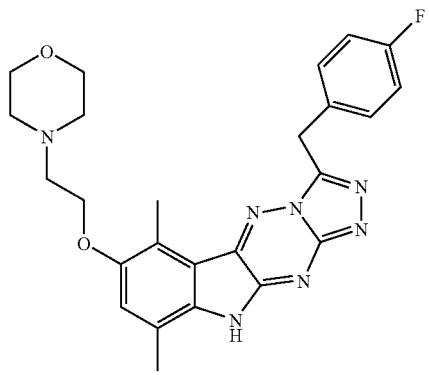

A reaction analogous to that in Example 36 using 5-(4-fluoro-benzyl)-[1,2,4]triazole-3,4-diamine as one of the reactants gave 3-(4-Fluoro-benzyl)-5,8-dimethyl-6-(2-morpholin-4-yl-ethoxy)-9H-1,2,3a,4,9,10-hexaaza-cyclopenta[b]fluorine (28%) as a pink solid.

$^1$H-NMR (400 MHz, DMSO-d$_6$) δ 11.91 (s, 1H), 7.42 (m, 2H), 7.20 (s, 1H), 7.12 (m, 2H), 4.51 (s, 2H), 4.11 (t, 2H), 3.58 (t, 4H), 2.72 (t, 2HO, 2.60 (s, 3H), 2.49 (m, 4H), 2.41 (s, 3H). MS (m/z) 476 [M+1].

Example 37

4-[6-(2-Diethylamino-ethyl)-5,8-dimethyl-9H-1,2,3a,4,9,10-hexaaza-cyclopenta[b]fluoren-3-ylmethyl]-phenol hydrochloride

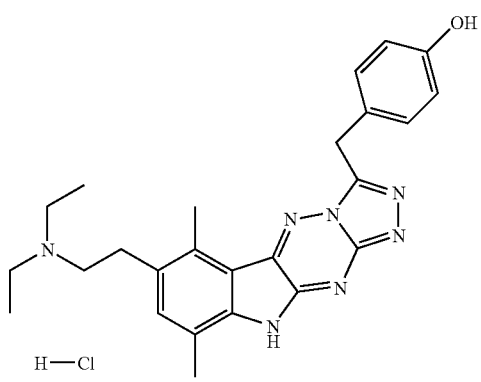

0.60 mmol of 5-(2-Diethylamino-ethyl)-4,7-dimethyl-1H-indole-2,3-dione hydrochloride (186.5 mg) and 0.70 mmol of 4-(4,5-diamino-4H-[1,2,4]triazol-3-ylmethyl)-phenol (144 mg) in 1.5 mL of ethylene glycol was stirred at 125° C. for 1 day. The mixture was cooled to room temperature, diluted with water (5 mL), stirred for 10 min. Allowed to crystallize in a refrigerator (+5° C.) overnight. The precipitated product was collected by filtration, washed with water (3×1 mL) and dried on high vacuum.

Y=206 mg of a brownish-orange solid (71.5%).

MS+cAPSCI: 444 (M+1).

MS−cAPCI: 442 (M−1).

$^1$H-NMR(DMSO-d$_6$, 400 MHz): δ 12.101 (s, 1H), 10.471 (br s, 1H), 9.293 (s, 1H) 7.346 (s, 1H), 7.188 (app d, J=8.2 Hz, 2H), 6.676 (app d, J=8.2 Hz, 2H), 4.389 (s, 2H), 3.231–3.131 (br m, 8H), 2.790 (s, 3H), 2.394 (s, 3H), 1.287 (t, J=7.4 Hz, 6H).

Example 38

4-[5,8-Dimethyl-6-(2-morpholin4-yl-ethyl)-9H-1,2,3a,4,9,10-hexaaza-cyclopenta[b]fluoren-3-ylmethyl]-phenol hydrochloride

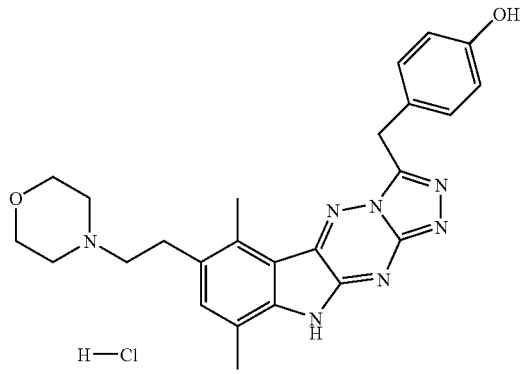

According to the procedure for Example 37, 0.60 mmol of 5-(N-morpholino-2-ethyl)-4,7-dimethyl-1H-indole-2,3-dione (195 mg) and 0.70 mmol of 4-(4,5-diamino4H-[1,2,4]triazol-3-ylmethyl)-phenol (144 mg) in 1.5 mL of ethylene glycol was stirred at 125° C. for 1 day. Y=207.5 mg of a biege solid (70%).

MS+cAPSCI: 458 (M+1).

MS−cAPCI: 456 (M−1).

$^1$H-NMR(DMSO-d$_6$, 400 MHz): δ 12.099 (br s, 1H), 9.279 (s, 1H) 7.321 (s, 1H), 7.191 (app d, J=8.2 Hz, 2H), 6.674 (app d, J=8.2 Hz, 2H), 4.398 (s, 2H), 3.833 (br m, 6H), 3.115 (br m, 6H) 2.793 (s, 3H), 2.404 (s, 3H).

Example 39

4-[5,8-Dimethyl-6-(2-pyrrolidin-1-yl-ethyl)-9H-1,2,3a,4,9,10-hexaaza-cyclopenta[b]fluoren-3-ylmethyl]-phenol hydrochloride

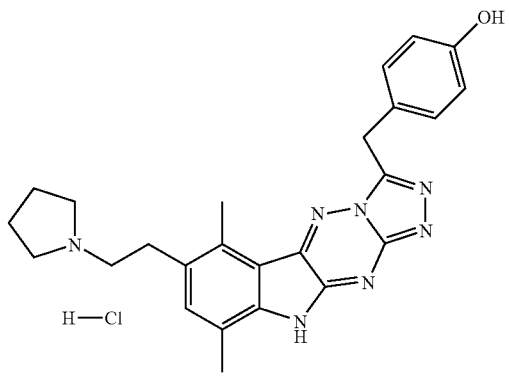

According to the procedure for Example 37, 0.60 mmol of 5-(N-pyrrolidino-2-ethyl)-4,7-dimethy-1H-indole-2,3-dione (185.5 mg) and 0.70 mmol of 4-(4,5-diamino4H-[1,2,4]triazol-3-ylmethyl)-phenol (144 mg) in 1.5 mL of ethylene glycol was stirred at 125° C. for 1 day. Y=191 mg of a biege solid (66.5%).

MS+cAPSCI: 442 (M+1).

MS−cAPCI: 440 (M−1).

$^1$H-NMR(DMSO-d$_6$, 400 MHz): δ 12.102 (br s, 1H), 10.653 (br s, 1H), 9.281 (s, 1H) 7.348 (s, 1H), 7.190 (app d, J=8.2 Hz, 2H), 6.674 (app d, J=8.2 Hz, 2H), 4.397 (s, 2H), 3.583 (very br m, 2H), 3.278 (br m, 2H), 3.098 (br m, 4H), 2.790 (s, 3H), 2.403 (s, 3H), 2.012 (br m, 2H), 1.940 (br m, 2H).

Example 40

3-(4-Fluoro-benzyl)-5,8-dimethyl-6-(2-morpholin-4-yl-ethyl)-9H-1,2,3a,4,9,10-hexaaza-cyclopenta[b]fluorine hydrochloride

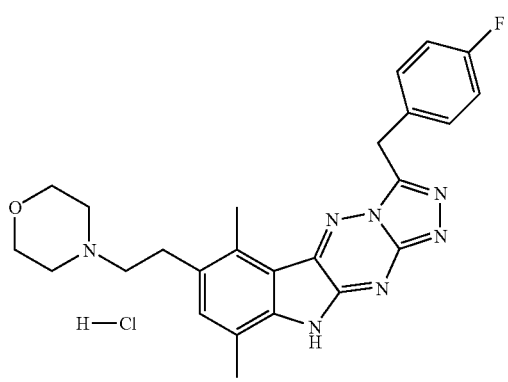

According to the procedure for Example 37, 0.60 mmol of 5-(N-morpholino-2-ethyl)-4,7-dimethyl-1H-indole-2,3-dione hydrochloride (195 mg) and 0.70 mmol of (4-fluoro-benzyl)-[1,2,4]triazole-3,4-diamine (145 mg) in 1.5 mL of ethylene glycol was stirred at 125° C. for 1 day.

Y=149 mg of an orange solid (50%).

MS+cAPSCI: 460 (M+1).

$^1$H-NMR(DMSO-d$_6$, 400 MHz): δ 12.092 (br s, 1H), 7.433 (app dd, J=8.7 Hz, J=5.5 Hz, 2H), 7.315 (s, 1H), 7.125 (app t, J=9.0 Hz, 2H), 4.532 (s, 2H), 3.757 (very br m, 4H), 3.027 (very br m, 8H), 2.753 (s, 3H), 2.400 (s, 3H); $^9$F-NMR(DMSO-d$_6$, 376.5 MHz): δ-116.38 (m, 1F).

Example 41

3-(4-Fluoro-benzyl)-5,8-dimethyl-6-(2-pyrrolidin-1-yl-ethyl)-9H-1,2,3a,4,9,10-hexaaza-cyclopenta[b]fluorine hydrochloride

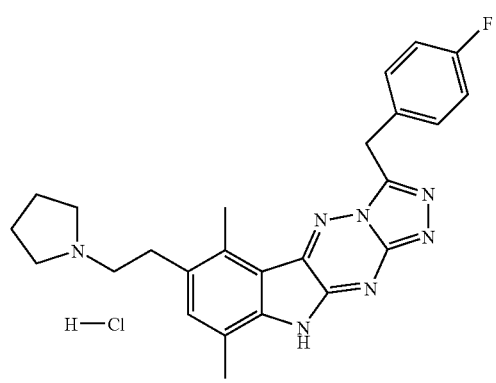

According to the procedure for Example 37, 0.60 mmol of 5-(N-pyrrolidino-2-ethyl)-4,7-dimethyl-1H-indole-2,3-dione hydrochloride (185.5 mg) and 0.70 mmol of (4-fluoro-benzyl)-[1,2,4]triazole-3,4-diamine (145 mg) in 1.5 mL of ethylene glycol was stirred at 125° C. for 1 day.

Y=87 mg of an orange solid (30%).

MS+cAPSCI: 444 (M+1).

MS−cAPCI: 442 (M−1).

$^1$H-NMR(DMSO-d$_6$, 400 MHz): δ 12.136 (s, 1H), 10.674 (br s, 1H), 7.433 (app dd, J=8.6 Hz, J=5.5 Hz, 2H), 7.364 (s, 1H), 7.125 (app t, J=9.0 Hz, 2H), 4.539 (s, 2H), 3.584 (br m, 2H), 3.268 (br m, 2H), 2.771 (s, 3H), 2.410 (s, 3H), 2.037 (br m, 2H), 1.909 (br m, 2H), $^{19}$F-NMR (DMSO-d$_6$, 376.5 MHz): δ-116.36 (m, 1F).

Example 42

Diethyl-{2-[3-(4-fluoro-benzyl)-5,8-dimethyl-9H-1,2,3a,4,9,10-hexaaza-cyclopenta[b]fluoren-6-yl]-ethyl}-amine hydrochloride

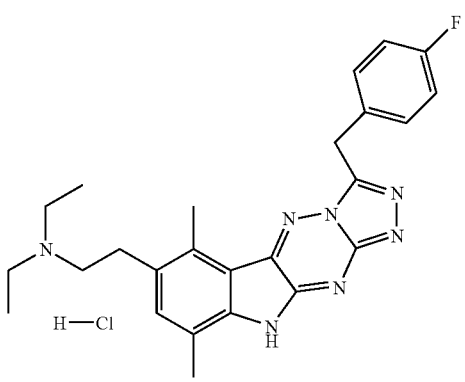

0.60 mmol of 5-(N,N-diethylamino-2-ethyl)-4,7-dimethyl-1H-indole-2,3-dione hydrochloride (186.5 mg) and 0.70 mmol of (4-fluoro-benzyl)-[1,2,4]triazole-3,4-diamine (145 mg) in 1.5 mL of ethylene glycol was stirred at 125° C. for 1 day. The mixture was cooled to room temperature, diluted with water (5 mL), and neat diethylamine 0.5 mL was added. Stirred for 3 hours, the precipitate was collected by filtration, washed with water and dried on highvac. The obtained free base was suspended in water (10 mL), 2M HCl 0.5 mL was added, heated to boil, sonicated briefly while hot and then allowed to crystallize in a refrigerator (+5° C.) overnight. The precipitate was collected by filtration, washed with ice-cold water (2×1 mL) and dried on high vacuum.

Y=172 mg of an orange-biege solid (59.5%).
MS+cAPCI: 446 (M+1).
MS−cAPCI: 444 (M−1).
$^1$H-NMR(DMSO-d$_6$, 400 MHz): δ 12.135 (s, 1H), 10.374 (br s, 1H), 7.432 (app dd, J=8.6 Hz, J=3.1 Hz, 2H), 7.375 (s, 1H), 7.125 (app t, J=9.0 Hz, 2H), 4.534 (s, 2H), 3.226 (br m, 4H), 3.133 (br m, 4H), 2.777 (s, 3H), 2.408 (s, 3H), 1.282 (t, J=7.4 Hz, 6H); $^{19}$F-NMR(DMSO-d$^6$, 376.5 MHz): δ-116.37 (m, 1F).

Biological Examples

The following assays are employed to find those compounds demonstrating the optimal degree of the desired activity.

Assay Procedures.

The following assays may be used to determine the level of activity and effect of the different compounds of the present invention on one or more of the PKs. Similar assays can be designed along the same lines for any PK using techniques well known in the art.

Several of the assays described herein are performed in an ELISA (Enzyme-Linked Immunosorbent Sandwich Assay) format (Voller, et al., 1980, "Enzyme-Linked Immunosorbent Assay," Manual of Clinical Immunology, 2d ed., Rose and Friedman, Am. Soc. Of Microbiology, Washington, D.C., pp. 359–371). The general procedure is as follows: a compound is introduced to cells expressing the test kinase, either naturally or recombinantly, for a selected period of time after which, if the test kinase is a receptor, a ligand known to activate the receptor is added. The cells are lysed and the lysate is transferred to the wells of an ELISA plate previously coated with a specific antibody recognizing the substrate of the enzymatic phosphorylation reaction. Non-substrate components of the cell lysate are washed away and the amount of phosphorylation on the substrate is detected with an antibody specifically recognizing phosphotyrosine compared with control cells that were not contacted with a test compound.

The presently preferred protocols for conducting the ELISA experiments for specific PKs is provided below. However, adaptation of these protocols for determining the activity of compounds against other RTKs, as well as for CTKs and STKs, is well within the scope of knowledge of those skilled in the art. Other assays described herein measure the amount of DNA made in response to activation of a test kinase, which is a general measure of a proliferative response. The general procedure for this assay is as follows: a compound is introduced to cells expressing the test kinase, either naturally or recombinantly, for a selected period of time after which, if the test kinase is a receptor, a ligand known to activate the receptor is added. After incubation at least overnight, a DNA labeling reagent such as 5-bromodeoxyuridine (BrdU) or H$^3$-thymidine is added. The amount of labeled DNA is detected with either an anti-BrdU antibody or by measuring radioactivity and is compared to control cells not contacted with a test compound.

MET Transphosphorylation Assay

This assay is used to measure phosphotyrosine levels on a poly(glutamic acid:tyrosine (4:1)) substrate as a means for identifying agonists/antagonists of met transphosphorylation of the substrate.

Materials and Reagents:

1. Corning 96-well Elisa plates, Corning Catalog #25805-96.
2. Poly(glu, tyr) 4:1, Sigma, Cat. No; P 0275.
3. PBS, Gibco Catalog #450-1300EB
4. 50 mM HEPES
5. Blocking Buffer: Dissolve 25 g Bovine Serum Albumin, Sigma Cat. No A-7888, in 500 ml PBS, filter through a 4 μm filter.
6. Purified GST fusion protein containing the Met kinase domain, Sugen, Inc.
7. TBST Buffer.
8. 10% aqueous (MilliQue H$_2$O) DMSO.
9. 10 mM aqueous (dH$_2$O) Adenosine-5'-triphosphate, Sigma Cat. No. A-5394.
10. 2× Kinase Dilution Buffer: for 100 ml, mix 10 mL 1M HEPES at pH 7.5 with 0.4 mL 5% BSA/PBS, 0.2 mL 0.1M sodium orthovanadate and 1 mL 5M sodium chloride in 88.4 mL dH$_2$O.
11. 4× ATP Reaction Mixture: for 10 mL, mix 0.4 mL 1M manganese chloride and 0.02 mL 0.1M ATP in 9.56 mL dH$_2$O.
12. 4× Negative Controls Mixture: for 10 mL, mix 0.4 mL 1M manganese chloride in 9.6 mL dH$_2$O.
13. NUNC 96-well V bottom polypropylene plates, Applied Scientific Catalog #S-72092
14. 500 mM EDTA.
15. Antibody Dilution Buffer: for 100 mL, mix 10 mL 5% BSA/PBS, 0.5 mL 5% Carnation Instant Milk® in PBS and 0.1 mL 0.1M sodium orthovanadate in 88.4 mL TBST.
16. Rabbit polyclonal antophosphotyrosine antibody, Sugen, Inc.
17. Goat anti-rabbit horseradish peroxidase conjugated antibody, Biosource, Inc.
18. ABTS Solution: for 1 L, mix 19.21 g citric acid, 35.49 g Na$_2$HPO$_4$ and 500 mg ABTS with sufficient dH$_2$O to make 1 L.
19. ABTS/H$_2$O$_2$: mix 15 mL ABST solution with 2 μL H$_2$O$_2$ five minutes before use.
20. 0.2M HCl Procedure:

1. Coat ELISA plates with 2 μg Poly(Glu-Tyr) in 100 μL PBS, store overnight at 4° C.
2. Block plate with 150 μL of 5% BSA/PBS for 60 min.
3. Wash plate twice with PBS, once with 50 mM Hepes buffer pH 7.4.
4. Add 50 μl of the diluted kinase to all wells. (Purified kinase is diluted with Kinase Dilution Buffer. Final concentration should be 10 ng/well.)
5. Add 25 μL of the test compound (in 4% DMSO) or DMSO alone (4% in dH$_2$O) for controls to plate.
6. Incubate the kinase/compound mixture for 15 minutes.
7. Add 25 μL of 40 mM MnCl$_2$ to the negative control wells.
8. Add 25 μL ATP/MnCl$_2$ mixture to the all other wells (except the negative controls). Incubate for 5 min.
9. Add 25 μL 500 mM EDTA to stop reaction.

10. Wash plate 3× with TBST.
11. Add 100 µL rabbit polyclonal anti-Ptyr diluted 1:10,000 in Antibody Dilution Buffer to each well. Incubate, with shaking, at room temperature for one hour.
12. Wash plate 3× with TBST.
13. Dilute Biosource HRP conjugated anti-rabbit antibody 1: 6,000 in Antibody Dilution buffer. Add 100 µL per well and incubate at room temperature, with shaking, for one hour.
14. Wash plate 1× with PBS.
15. Add 100 µl of ABTS/$H_2O_2$ solution to each well.
16. If necessary, stop the development reaction with the addition of 100 µl of 0.2M HCl per well.
17. Read plate on Dynatech MR7000 elisa reader with the test filter at 410 nM and the reference filter at 630 nM.

MET Transphosphorylation Assay Results:

Table 1 shows the $IC_{50}$ values obtained for a number of compounds of the preferred embodiments of the invention.

TABLE 1

| Compound | Example Number | c-MET $IC_{50}$ (µM) |
|---|---|---|
|  | 17 | 0.018 |
|  | 18 | 0.036 |
|  | 19 | 0.012 |

TABLE 1-continued

| Compound | Example Number | c-MET IC$_{50}$ (µM) |
|---|---|---|
| (structure) | 20 | 0.046 |
| (structure) | 21 | 0.01 |
| (structure) | 22 | 0.035 |
| (structure) | 23 | 0.46 |

TABLE 1-continued

| Compound | Example Number | c-MET IC$_{50}$ (μM) |
|---|---|---|
| | 24 | 0.022 |
| | 25 | 0.055 |
| | 26 | 0.025 |
| | 34 | 0.042 |

TABLE 1-continued

| Compound | Example Number | c-MET IC$_{50}$ (μM) |
|---|---|---|
| (structure) | 35 | 0.028 |
| (structure) | 36 | 0.56 |

One skilled in the art would readily appreciate that the present invention is well adapted to carry out the objects and obtain the ends and advantages mentioned, as well as those inherent herein. The molecular complexes and the methods, procedures, treatments, molecules, specific compounds described herein are presently representative of preferred embodiments, are exemplary, and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

What is claimed is:

1. A compound of the formula I:

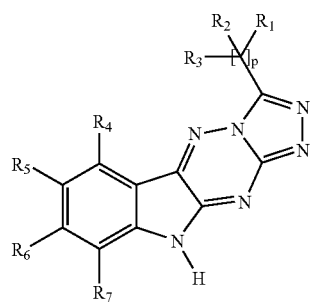

wherein:

$R_1$ is an aryl or heteroaryl group, wherein said aryl or heteroaryl group is unsubstituted or optionally substituted with one or more substituents selected from the group consisting of halogen, —OH, —OR$_8$, —COR$_8$, —COOR$_8$, —CONR$_8$R$_9$, —NR$_8$R$_9$, —CN, —NO$_2$, —S(O)$_2$R$_8$, —SO$_2$NR$_8$R$_9$, —CF$_3$, lower alkyl, cycloalkyl, heterocycle, alkenyl, alkynyl and aryl;

each $R_2$ and $R_3$ is independently selected from the group consisting of hydrogen halogen, —OH, —OR$_7$, —NR$_7$R$_8$, —CN, —COR$_8$, —COOR$_8$, —CONR$_8$R$_9$, —OF$_3$, lower alkyl, cycloalkyl, heterocycle, alkenyl and alkynyl; or $R_2$ and $R_3$, together with the carbon atom to which they are attached can form a cycloalkyl or heterocycle;

$R_4$, $R_5$, $R_6$, and $R_7$ are independently selected from the group consisting of hydrogen, halogen, —OR$_8$, —COR$_8$, —COOR$_8$, —CONR$_8$R$_9$, —NR$_8$R$_9$, —ON, —NO$_2$, —S(O)$_n$R$_8$ (wherein n is 0, 1 or 2), —SO$_2$R$_7$R$_8$, —CF$_3$, lower alkyl, cycloalkyl, heterocycle, alkenyl, alkynyl, and aryl;

each $R_8$ and $R_9$ is independently selected from the group consisting of hydrogen, lower alkyl, cycloalkyl, heterocycle, alkenyl, alkynyl, aryl, aminoalkyl, alkylaminoalkyl, and dialkylaminoalkyl, or $R_8$ and $R_9$ together with the atom to which they are attached form a heteroalicyclic ring optionally substituted with a group selected from the group consisting of alkyl, —OH and amino; and p is 1, 2, 3, 4 or 5, it being understood that when p is greater than 1, the $R_2$ and $R_3$ groups on each carbon atom may be the same as or different from the $R_2$ and $R_3$ groups on any adjacent carbon atom; or a pharmaceutically acceptable salt thereof.

2. The compound of claim 1, wherein p is 1.

3. The compound of claim 1, wherein $R_1$ is phenyl.

4. The compound of claim 3, wherein said phenyl group is substituted with an —OH or a halo group.

5. A compound of formula II:

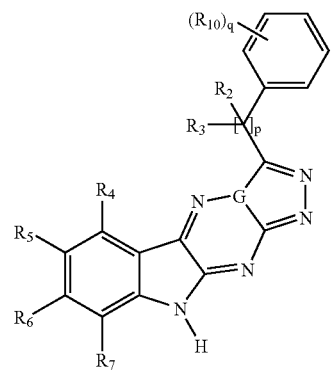

wherein:

each $R_{10}$ is independently selected from the group consisting of halogen, —OH, —OR$_8$, —COR$_8$, —COOR$_8$, —CONR$_8$R$_9$, —NR$_8$R$_9$, —CN, —NO$_2$, —S(O)$_2$R$_8$, —SO$_2$NR$_8$R$_9$, —CF$_3$, lower alkyl, cycloalkyl, heterocycle, alkenyl, alkynyl and aryl;

q is 1, 2, 3, 4 or 5;

G is nitrogen or carbon;

each $R_2$ and $R_3$ is independently selected from the group consisting of hydrogen, halogen, —OH, —OR$_7$, —NR$_7$R$_8$, —CN, —COR$_8$, —COOR$_8$, —CONR$_8$R$_9$, —CF$_3$, lower alkyl, cycloalkyl, heterocycle, alkenyl and alkynyl; or $R_2$ and $R_3$, together with the carbon atom to which they are attached can form a cycloalkyl or heterocycle;

$R_4$, $R_5$, $R_6$, and $R_7$ are independently selected from the group consisting of hydrogen, halogen, —OR$_8$, —COR$_8$, —COOR$_8$, —CONR$_8$R$_9$, —NR$_8$R$_9$, —CN, —NO$_2$, —S(O)$_n$R$_8$ (wherein n is 0, 1 or 2), —SO$_2$R$_8$R$_9$, —CF$_3$, lower alkyl, cycloalkyl, heterocycle, alkenyl, alkynyl, and aryl; and $R_8$ and $R_9$ are selected from the group consisting of hydrogen, lower alkyl, cycloalkyl, heterocycle, alkenyl, alkynyl, aryl, aminoalkyl, alkylaminoalkyl, and dialkylaminoalkyl, or $R_8$ and $R_9$ together with the atom to which they are attached form a heteroalicyclic ring optionally substituted with a group selected from the group consisting of alkyl, —OH and amino; and p is 1, 2, 3, 4 or 5, it being understood that when p is greater than 1, the $R_2$ and $R_3$ groups on each carbon atom may be the same as or different from the $R_2$ and $R_3$ groups on any adjacent carbon atom; or a pharmaceutically acceptable salt thereof.

6. The compound of claim 5, wherein the variable p is 1.

7. The compound of claim 5, wherein $R_{10}$ is —OH or halo and q is 1.

8. The compound of claim 5, wherein the variable G is nitrogen.

9. A compound selected from the group consisting of:
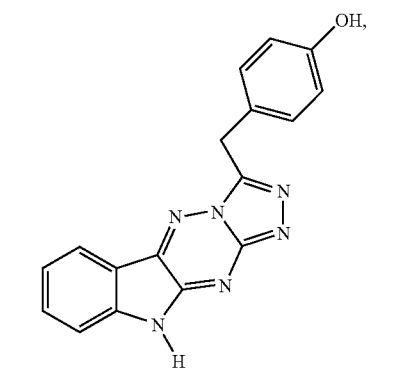
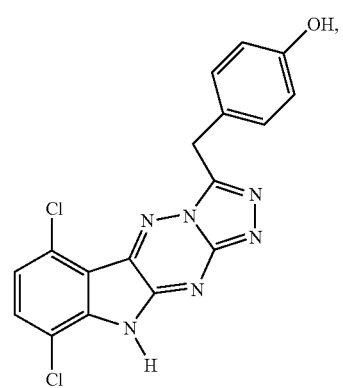
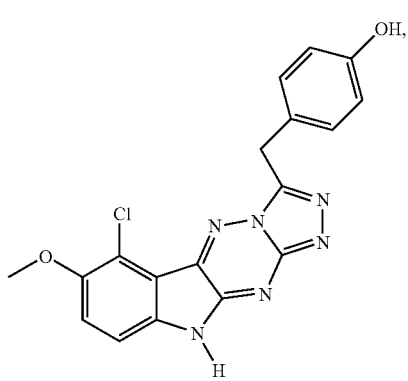
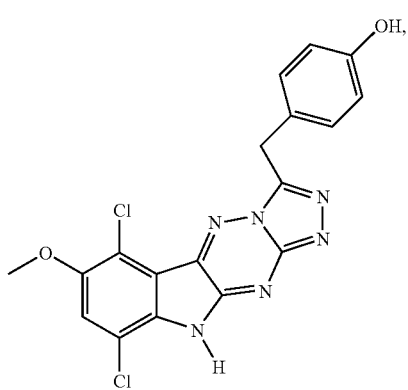
-continued
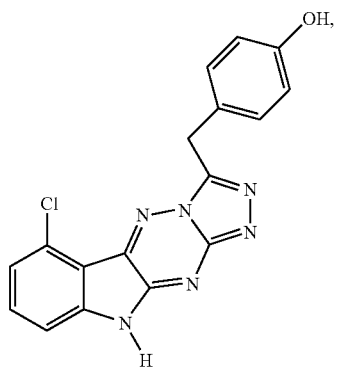
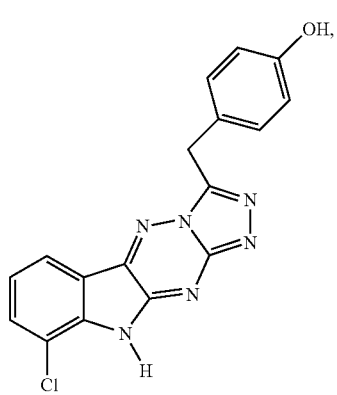
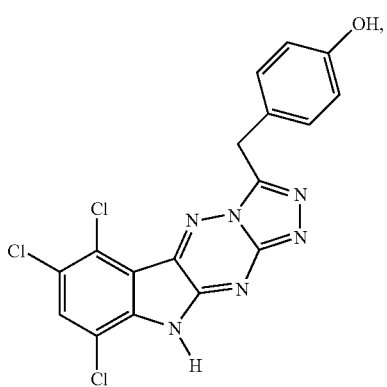
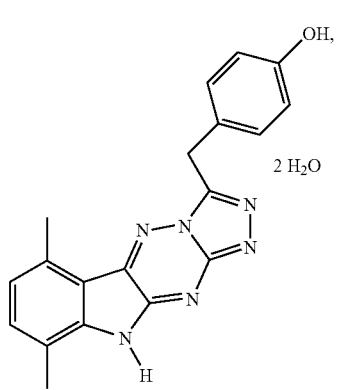
2 H₂O

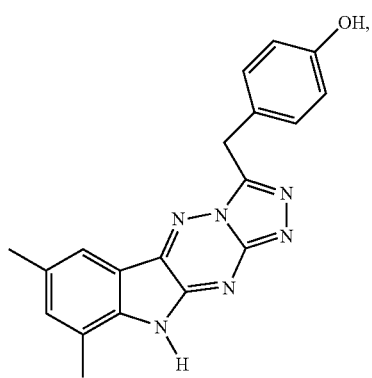
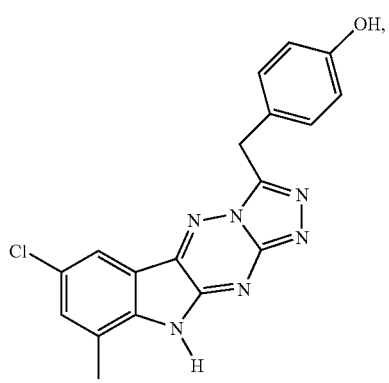
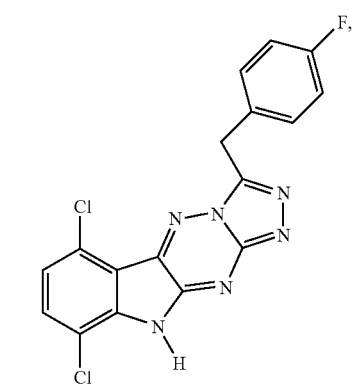
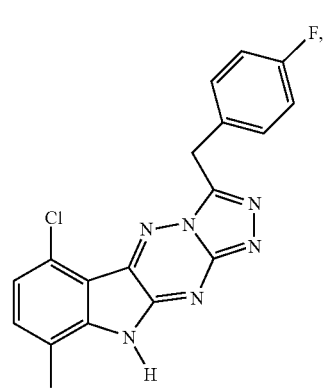
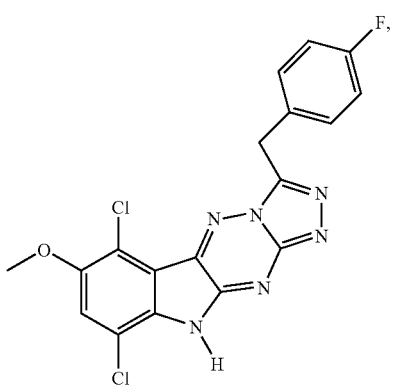
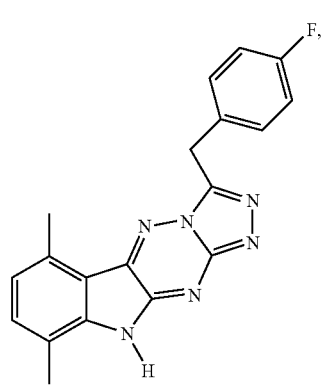
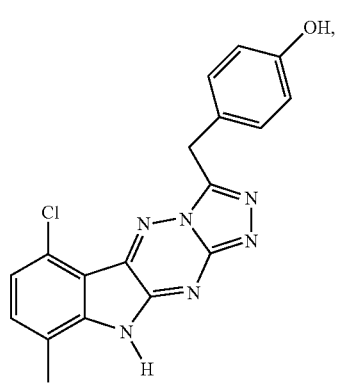
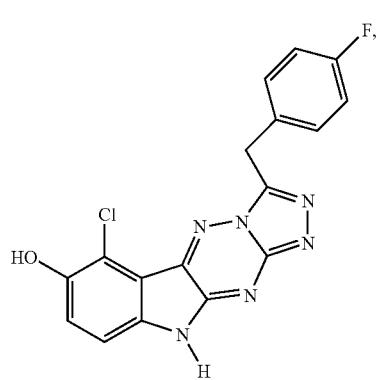

-continued
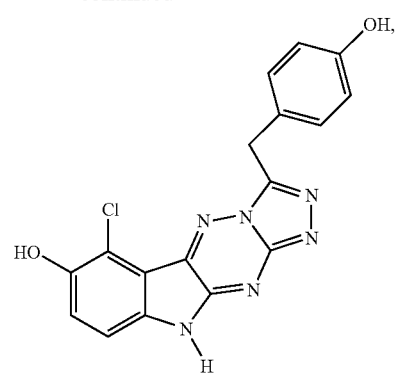
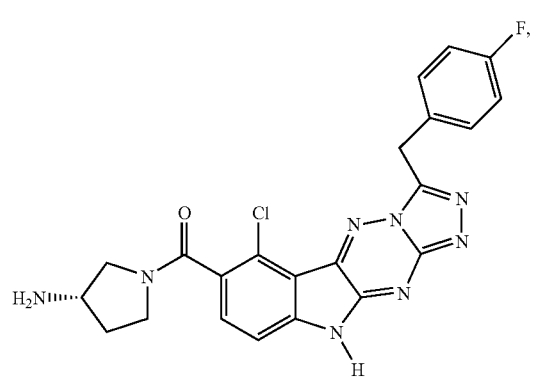
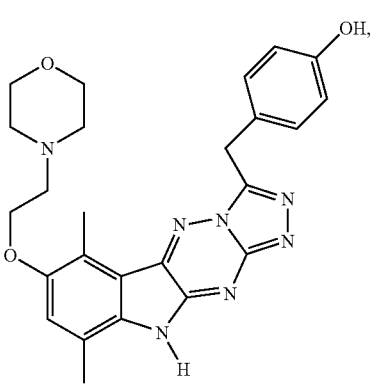
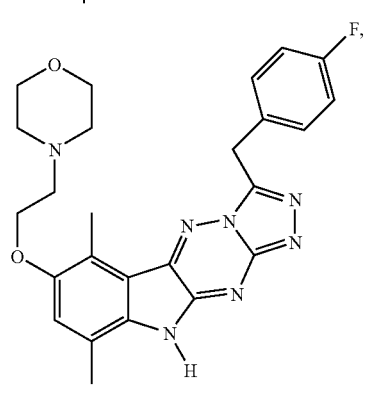
-continued
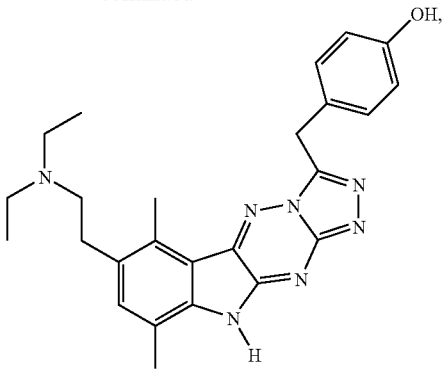
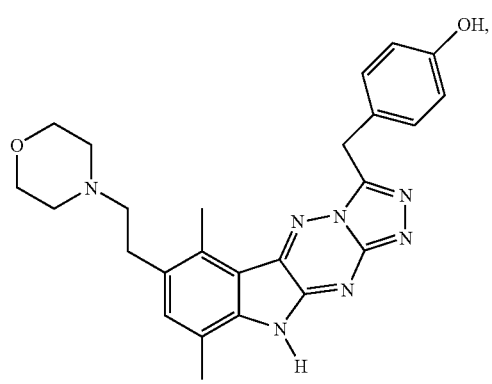
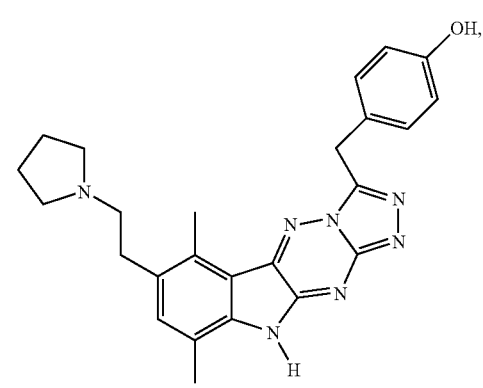
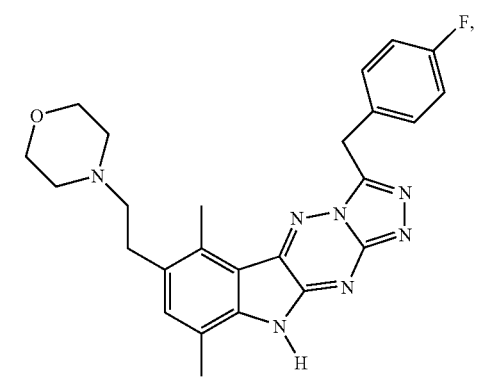

-continued
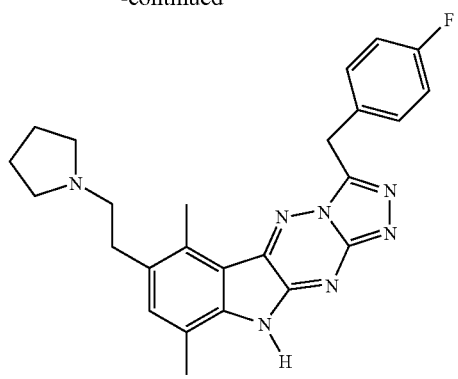
and
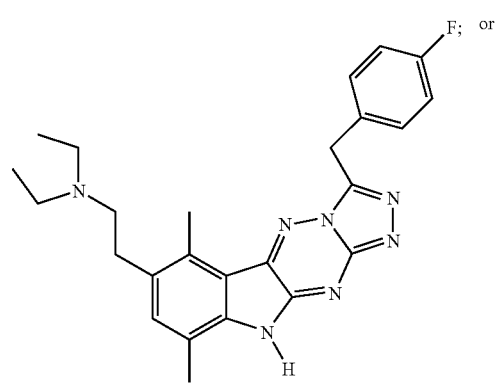
a pharmaceutically acceptable salt thereof.
10. A compound which is:
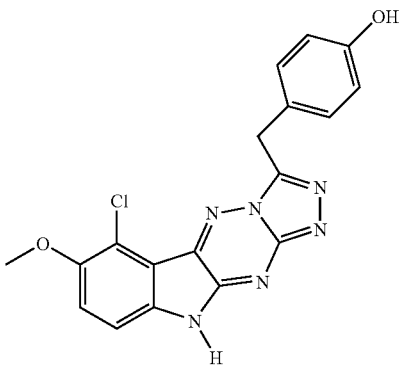
or
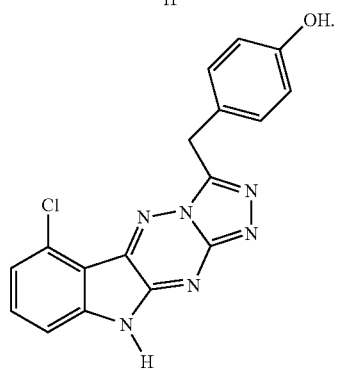
11. A pharmaceutical composition comprising a compound of claim 1, or pharmaceutically acceptable salt thereof, and a pharmaceutically acceptable carrier or excipient.
* * * * *